US012588887B2

(12) United States Patent　　　　(10) Patent No.:　US 12,588,887 B2
Graveley et al.　　　　　　　　　　(45) Date of Patent:　Mar. 31, 2026

(54) MEDICAL DEVICE POSITION SENSING COMPONENTS

(71) Applicant: Boston Scientific Scimed, Inc., Maple Grove, MN (US)

(72) Inventors: Andrew Brian Graveley, Shoreview, MN (US); Daniel J. Foster, Lino Lakes, MN (US); Sebastian Ordas Carboni, Vadnais Heights, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 191 days.

(21) Appl. No.: 18/335,213

(22) Filed: Jun. 15, 2023

(65) Prior Publication Data

US 2023/0404521 A1　Dec. 21, 2023

Related U.S. Application Data

(60) Provisional application No. 63/366,538, filed on Jun. 17, 2022.

(51) Int. Cl.
　*A61B 8/08*　　　(2006.01)
　*A61B 17/34*　　(2006.01)
　*A61B 34/20*　　(2016.01)
(52) U.S. Cl.
　CPC ........ *A61B 8/0841* (2013.01); *A61B 17/3403* (2013.01); *A61B 34/20* (2016.02);
(Continued)
(58) Field of Classification Search
　CPC ... A61B 8/0841; A61B 17/3403; A61B 34/20; A61B 2017/3413; A61B 2034/2051;
(Continued)

(56) References Cited

U.S. PATENT DOCUMENTS

| | | | |
|---|---|---|---|
| 4,944,308 | A | 7/1990 | Kerfeldt |
| 5,842,999 | A | 12/1998 | Pruitt et al. |

(Continued)

FOREIGN PATENT DOCUMENTS

| | | |
|---|---|---|
| CA | 2836019 A1 | 6/2014 |
| EP | 2364120 A1 | 9/2011 |

OTHER PUBLICATIONS

International Search Report and Written Opinion in PCT/US2023/025360, dated Oct. 4, 2022 (10 pages).
(Continued)

*Primary Examiner* — Michael J Carey
*Assistant Examiner* — Zainab Mohammed Aldarraji
(74) *Attorney, Agent, or Firm* — Bookoff McAndrews, PLLC

(57) ABSTRACT

A medical device is described that may include a handle and a needle extending distally from the handle. The needle may be configured to be at least partially inserted into a body, and may include a sheath and a core disposed in the sheath. The core may have a distal portion including a distal tip, and a proximal portion distinct from the distal portion. A proximal end of the distal portion may be coupled to a distal end of the proximal portion to define a cavity between the proximal end of the distal portion and the distal end of the proximal portion. The needle may further include a device of a position sensing system arranged in the cavity. The device may be a transmitter device or a receiver device. The position sensing system may be configured to determine a position or an orientation of the distal tip.

20 Claims, 10 Drawing Sheets

(52) U.S. Cl.
CPC ................. *A61B 2017/3413* (2013.01); *A61B 2034/2051* (2016.02)

(58) Field of Classification Search
CPC ........ A61B 2010/0208; A61B 10/0275; A61B 34/25; A61B 2090/365; A61B 8/4254
See application file for complete search history.

(56) References Cited

U.S. PATENT DOCUMENTS

| | | | |
|---|---|---|---|
| 5,989,196 A | 11/1999 | Chu et al. | |
| 9,968,338 B2 | 5/2018 | Shabaz | |
| 10,782,114 B2 | 9/2020 | Hein et al. | |
| 2008/0132911 A1 | 6/2008 | Sobe | |
| 2012/0143029 A1 | 6/2012 | Silverstein et al. | |
| 2013/0131597 A1* | 5/2013 | Blaivas | A61M 25/0097 |
| | | | 604/173 |
| 2013/0296691 A1* | 11/2013 | Ashe | A61B 5/6848 |
| | | | 600/424 |
| 2017/0035515 A1 | 2/2017 | Hautvast et al. | |
| 2017/0188881 A1 | 7/2017 | Hein et al. | |
| 2017/0188882 A1 | 7/2017 | Foster et al. | |
| 2018/0116643 A1 | 5/2018 | Bang et al. | |
| 2018/0168482 A1 | 6/2018 | Hein | |
| 2018/0168738 A1 | 6/2018 | Viswanathan et al. | |
| 2018/0172420 A1 | 6/2018 | Hein et al. | |
| 2018/0172865 A1 | 6/2018 | Hein et al. | |
| 2018/0220926 A1 | 8/2018 | Kelly et al. | |
| 2018/0220927 A1 | 8/2018 | Kelly et al. | |
| 2018/0220928 A1 | 8/2018 | Blood et al. | |
| 2018/0220929 A1 | 8/2018 | Blood et al. | |
| 2018/0224508 A1 | 8/2018 | Kelly et al. | |
| 2018/0289357 A1* | 10/2018 | Jensen | A61B 8/12 |
| 2019/0056242 A1 | 2/2019 | Foster et al. | |
| 2019/0056243 A1 | 2/2019 | Foster et al. | |
| 2019/0217059 A1 | 7/2019 | Meyer et al. | |
| 2019/0219647 A1 | 7/2019 | Foo et al. | |
| 2020/0007173 A1 | 1/2020 | Plotkin et al. | |
| 2020/0372409 A1 | 11/2020 | Srivastava et al. | |
| 2022/0087648 A1* | 3/2022 | Gran | A61B 8/445 |

OTHER PUBLICATIONS

U.S. Appl. No. 18/330,088, filed Jun. 6, 2023 (64 pages).
U.S. Appl. No. 18/297,132, filed Apr. 7, 2023 (48 pages).
U.S. Appl. No. 18/307,365, filed Apr. 26, 2023 (42 pages).

* cited by examiner

600

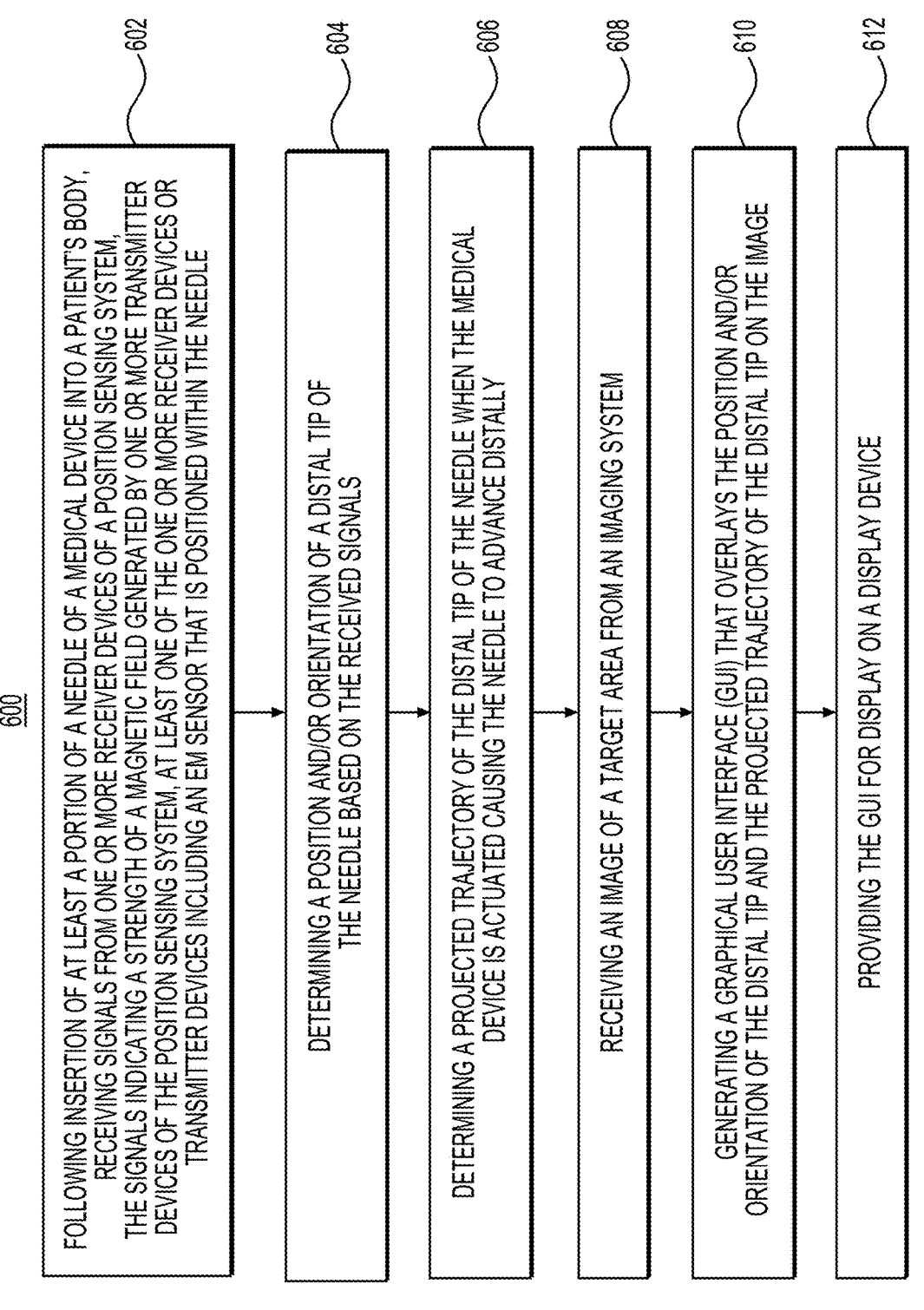

602 — FOLLOWING INSERTION OF AT LEAST A PORTION OF A MEDICAL DEVICE INTO A PATIENT'S BODY, RECEIVING SIGNALS FROM ONE OR MORE RECEIVER DEVICES OF A POSITION SENSING SYSTEM, THE SIGNALS INDICATING A STRENGTH OF A MAGNETIC FIELD GENERATED BY ONE OR MORE TRANSMITTER DEVICES OF THE POSITION SENSING SYSTEM, AT LEAST ONE OF THE ONE OR MORE RECEIVER DEVICES OR TRANSMITTER DEVICES INCLUDING AN EM SENSOR THAT IS POSITIONED WITHIN THE NEEDLE

604 — DETERMINING A POSITION AND/OR ORIENTATION OF A DISTAL TIP OF THE NEEDLE BASED ON THE RECEIVED SIGNALS

606 — DETERMINING A PROJECTED TRAJECTORY OF THE DISTAL TIP OF THE NEEDLE WHEN THE MEDICAL DEVICE IS ACTUATED CAUSING THE NEEDLE TO ADVANCE DISTALLY

608 — RECEIVING AN IMAGE OF A TARGET AREA FROM AN IMAGING SYSTEM

610 — GENERATING A GRAPHICAL USER INTERFACE (GUI) THAT OVERLAYS THE POSITION AND/OR ORIENTATION OF THE DISTAL TIP AND THE PROJECTED TRAJECTORY OF THE DISTAL TIP ON THE IMAGE

612 — PROVIDING THE GUI FOR DISPLAY ON A DISPLAY DEVICE

*FIG. 6*

MEDICAL DEVICE POSITION SENSING COMPONENTS

CROSS-REFERENCE TO RELATED APPLICATIONS

This application claims the benefit of priority from U.S. Provisional Application No. 63/366,538, filed on Jun. 17, 2022, which is incorporated by reference herein in its entirety.

TECHNICAL FIELD

The disclosure relates generally to devices, systems, and methods for medical device position sensing components. More specifically, aspects of the disclosure pertain to devices, systems, and/or methods for position sensing components integrated within and/or attached to medical devices for medical device position tracking.

BACKGROUND

Core needle biopsy devices are commonly used to acquire tissue samples to diagnose cancer, particularly in the prostate. Prostate biopsy procedures are typically guided under ultrasound, where an operator may control an ultrasound probe inserted within a patient's rectum with one hand and place a needle of the core needle biopsy outside of the perineum with the other hand. The needle may be spring loaded (e.g., in a retracted position) when placed. When the operator is ready to perform the biopsy, the operator may actuate a trigger device that causes the needle to advance forward from the retracted position to obtain a core sample of tissue.

Placing the needle under ultrasound is difficult and requires the operator to estimate spatial distances and orientation between the ultrasound probe inside the rectum and the needle outside the perineum. For example, the operator first estimates the trajectory of the needle based on the ultrasound image without any direct indication of where the needle is located relative to anatomy shown on the ultrasound image. Once the needle is inserted through the perineum, the operator aligns an ultrasound imaging plane to the needle tip in order to visualize the tip and place the needle in a desired location. However, if the needle is oblique to the ultrasound imaging plane, the operator may not see the needle tip, and many operators prefer an oblique approach so they can sample all regions of the prostate through a relatively smaller area of the perineum, and thus reduce the area they need to anesthetize prior to the procedure. Once the needle is visualized and placed in the desired location, the operator then estimates the three-dimensional trajectory of the needle when the needle advances forward from the retracted position to ensure a path that the needle will travel when advanced is only through tissue that can be safely biopsied. If the needle veers towards any critical anatomy, such as the rectal wall, urethra, seminal vesicles, or blood vessels, the needle may be advanced too quickly for the operator to track or correct course, causing the critical anatomy to be pierced, leading to complications for the patient.

SUMMARY

The present disclosure includes a medical device that may comprise a handle and a needle extending distally from the handle. The needle may be configured to be at least partially inserted into a body, and may include a sheath and a core disposed in the sheath. The core may have a distal portion including a distal tip, and a proximal portion distinct from the distal portion. A proximal end of the distal portion may be coupled to a distal end of the proximal portion to define a cavity between the proximal end of the distal portion and the distal end of the proximal portion. The needle may further include a device of a position sensing system arranged in the cavity, where the device is one of a transmitter device or a receiver device. The position sensing system may be configured to determine a position or an orientation of the distal tip.

In any of the exemplary medical devices disclosed herein, an interior surface of the proximal end of the distal portion of the core may include one or more interlocking features corresponding to one or more structural features of the distal end of the proximal portion to couple the distal portion to the proximal portion. The sheath and the core may be independently retractable into the handle, and only a distal end of the distal portion of the core may be exposed when the sheath is retracted proximally into the handle. The device of the position sensing system may be arranged in the cavity at a known distance and position relative to the distal tip.

In some aspects, the device of the position sensing system may be the receiver device, and the receiver device may comprise a magnetic field sensor configured to detect a magnetic field generated by an external transmitter device of the position sensing system, and provide a signal that indicates at least one of the position and the orientation of the distal tip based on a strength of the magnetic field detected. In other aspects, the device of the position sensing system may be the transmitter device, and the transmitter device may be configured to generate a magnetic field detectable by an external receiver device of the position sensing system, the external receiver device configured to provide a signal that indicates at least one of the position and the orientation of the distal tip based on a strength of the magnetic field detected.

A proximal end of the proximal portion of the core may be hollow to receive and direct wires of the device of the position sensing system into the handle. The handle may include an interposer board to which the wires are connected, the interposer board relaying signals between the wires and a controller of the position sensing system via an external cable connecting the interposer board and the controller. The handle may also include a compartment for receiving the wires of the device of the position sensing system from the proximal end of the proximal portion of the core. The wires may be housed in an internal cable within the compartment. The sheath and the core may be independently retractable into the handle, and the handle may further include a switch configured to detect when the core is in a retracted position in the handle. The switch may detect the core is in the retracted position, and signals may be provided to a computing device to cause generation and display of a graphical user interface, the graphical user interface comprising at least a projected needle trajectory for the needle that is overlaid on an image of a target area within the body. Once the needle is at least partially inserted in the body, the graphical user interface may be updated to further include at least one of the position and the orientation of the distal tip and a projected trajectory of the distal tip to the target area when the needle is advanced distally from the retracted position.

The medical device may be a component of a system further comprising the position sensing system and an ultrasound imaging system configured to generate ultrasound images in an ultrasound imaging plane. The ultrasound imaging system may include an ultrasound imaging console and an ultrasound probe. Another device of the position sensing system that is one of a transmitter device or a receiver device may be attachable to the ultrasound probe for determining at least one of the position and the orientation of the distal tip relative to the ultrasound imaging plane. When the device of the position sensing system arranged in the enclosed cavity is the receiver device, the other device of the position sensing system attached to the ultrasound probe may be the receiver device. When the device of the position sensing system arranged in the enclosed cavity is the transmitter device, the other device of the position sensing system attached to the ultrasound probe may be the transmitter device.

In another example, a medical device may comprise a needle and a handle from which the needle distally extends. The needle may be configured to be at least partially inserted into a body, and may include a sheath and a core disposed in the sheath. The core may have a distal portion including a distal tip, and a proximal portion distinct from the distal portion. A proximal end of the distal portion may be coupled to a distal end of the proximal portion to define a cavity between the proximal end of the distal portion and the distal end of the proximal portion. The needle may further include a device of a position sensing system arranged in the cavity, where the device is one of a transmitter device or a receiver device. The position sensing system may be configured to determine a position or an orientation of the distal tip. A proximal end of the proximal portion of the core may be hollow to receive and proximally direct wires of the device of the position sensing system. The handle may include a compartment for receiving wires of the device of the position sensing system proximally directed from the core.

Any of the exemplary medical devices disclosed herein may include any of the following features. The handle may further include an interposer board to which the wires of the device of the position sensing system are connected, the interposer board relaying signals between the wires and a controller of the position sensing system via an external cable connecting the interposer board and the controller. The sheath and the core may be independently retractable into the handle, and the handle may further include a switch connected to the interposer board, the switch configured to detect when the core is in a retracted position in the handle.

In another example, a medical device may comprise a handle and a needle extending distally from the handle. The needle may be configured to be at least partially inserted into a body toward a target area, and may include a sheath and a core disposed in the sheath. The core may have a distal portion including a distal tip, and a proximal portion distinct from the distal portion. A proximal end of the distal portion may be coupled to a distal end of the proximal portion to define a cavity between the proximal end of the distal portion and the distal end of the proximal portion. The needle may further include a device of a position sensing system arranged in the cavity, where the device is one of a transmitter device or a receiver device. The position sensing system may be configured to determine a position or an orientation of the distal tip of. The needle may be in a retracted position within the handle when the needle is at least partially inserted into the body toward the target area. A projected trajectory of the distal tip to the target area when the needle is advanced distally from the retracted position may be determined based on at least one of the position and the orientation of the distal tip. A graphical user interface overlaying at least one of the position and the orientation of the distal tip and the projected trajectory on an image of the target area may be generated and provided for display.

Any of the medical devices disclosed herein may have any of the following features. The medical device may be a component of a system further comprising the position sensing system and an ultrasound imaging system configured to generate the image of the target area in an ultrasound imaging plane. The ultrasound imaging system may comprise an ultrasound imaging console, and an ultrasound probe. Another device of the position sensing system that is one of a transmitter device or a receiver device may be attachable to the ultrasound probe for determining at least one of the position and the orientation of the distal tip relative to the ultrasound imaging plane.

It may be understood that both the foregoing general description and the following detailed description are exemplary and explanatory only and are not restrictive of the invention, as claimed. As used herein, the terms "comprises," "comprising," or any other variation thereof, are intended to cover a non-exclusive inclusion, such that a process, method, article, or apparatus that comprises a list of elements does not include only those elements, but may include other elements not expressly listed or inherent to such process, method, article, or apparatus. The term "exemplary" is used in the sense of "example," rather than "ideal." The term "distal" refers to a direction away from an operator/toward a treatment site, and the term "proximal" refers to a direction toward an operator. The term "approximately," or like terms (e.g., "substantially"), includes values +/−10% of a stated value.

BRIEF DESCRIPTION OF THE DRAWINGS

The accompanying drawings, which are incorporated in and constitute a part of this specification, illustrate examples of this disclosure and together with the description, serve to explain the principles of the disclosure.

FIG. 6 depicts an exemplary process to generate a graphical user interface to visualize a position and/or orientation of the medical device of FIGS. 1A and 1B.

DETAILED DESCRIPTION

Figures 1A, 1B:
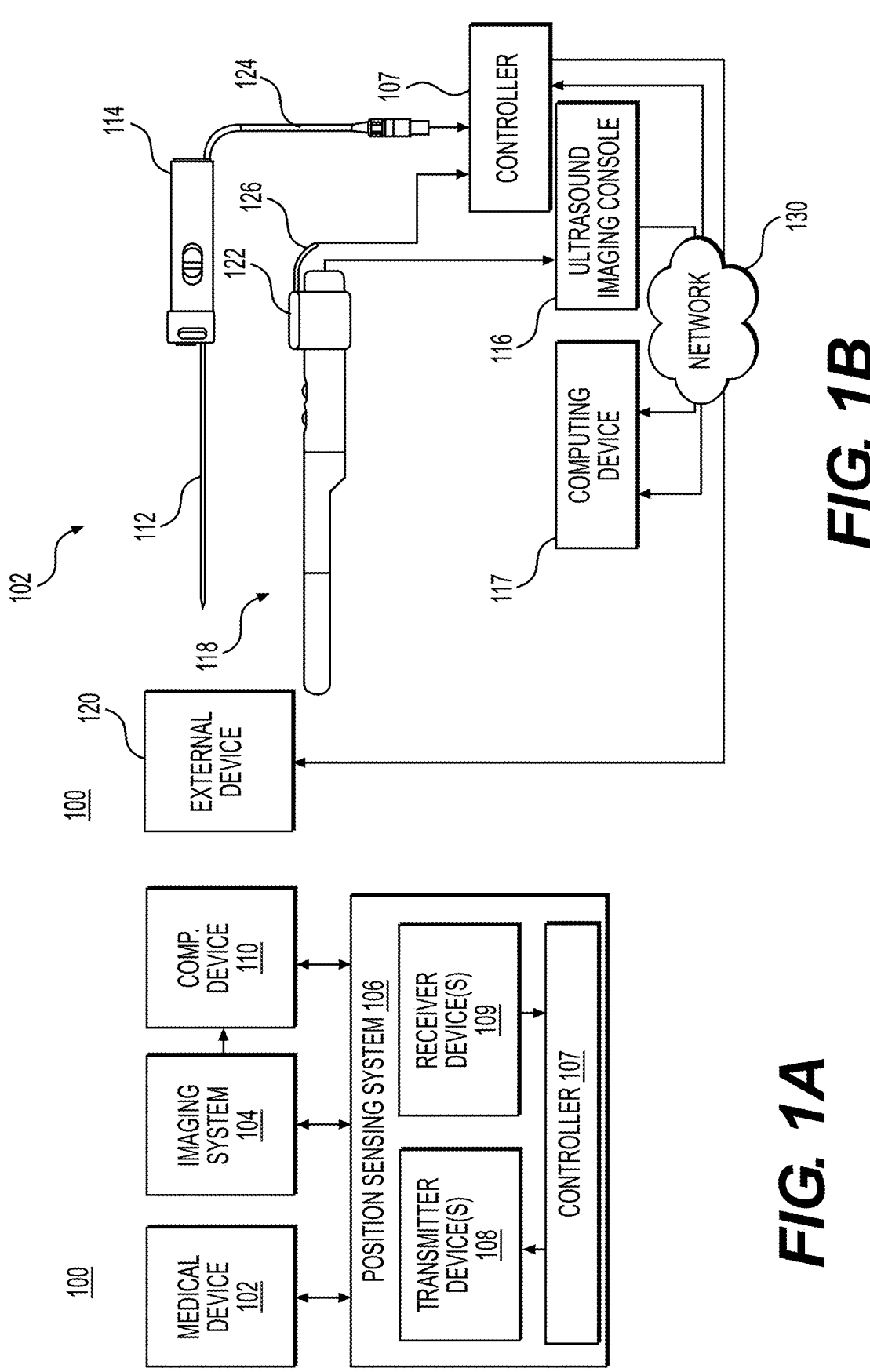
FIGS. 1A and 1B depict an exemplary system for performing an electromagnetic-navigated medical procedure using a medical device.

Electromagnetic ("EM")-navigated medical procedures may utilize EM tracking to provide information regarding a position and/or orientation of a medical device within a subject's anatomy, such as a position and/or orientation of a distal tip of a needle of a biopsy device. With EM tracking, position and/or orientation information may be fused with imaging (e.g., ultrasound imaging) performed before and during a procedure to generate and display graphical user interfaces for guiding the medical device through the subject's anatomy and provide a projected trajectory for the distal tip needle of the medical device when it is advanced distally from a retracted position to perform the biopsy to obtain a tissue sample.

The needle of the medical device may extend distally from a handle by which an operator holds the medical device, and may include a sheath and a core disposed within the sheath. The sheath and the core may be independently retractable into the handle, and may both be in a retracted position when the medical device is inserted into the body. The core may be comprised of two distinct portions, a distal portion and a proximal portion. The distal portion may include a distal tip and a proximal end of the distal portion may be coupled to a distal end of the proximal portion to define a cavity between the proximal end of the distal portion and the distal end of the proximal portion. The needle may further include a device of a position sensing system that is arranged in the cavity. In some aspects, the device may be a receiver device of the position sensing system comprising a magnetic field sensor. The magnetic field sensor may be configured to detect a magnetic field generated by an external transmitter device of the position sensing system, and provide a signal to a controller of the position sensing system that indicates the position and/or orientation of the distal tip of the needle based on a strength of the magnetic field detected. In other aspects, the device may be a transmitter device of the position sensing system configured to generate a magnetic field detectable by an external receiver device of the position sensing system, where the external receiver device may be configured to provide a signal to the controller that indicates that position and/or orientation of the distal tip of the needle based on a strength of the magnetic field detected. A proximal end of the proximal portion of the core may be hollow to receive and direct wires of the device of the position sensing system into the handle.

In addition to including components to enable the retraction of the sheath and core components of the needle into the handle and the subsequent advancement thereof, the handle of the medical device may include a compartment for receiving the wires of the device of the position sensing system to allow slack as the needle is retracted and advanced. The wires may be connected to an interposer board within the handle to relay signals between the wires and a controller of the position sensing system via an external cable of the medical device. The handle may also include a switch connected to the interposer board that is configured to detect when the needle is in a retracted position. When the retracted position is detected, signals may be provided via the interposer board to trigger an application executing on a computing device to generate and display a graphical interface for guiding the medical device. In some aspects, when the needle is positioned at least near the body (e.g., prior to insertion into the body), a projected needle trajectory may be determined by the position sensing system. A graphical user interface overlaying the projected needle trajectory on an image of the target area may be generated and displayed to allow an operator to visualize and plan a trajectory of the needle (e.g., to plan the path of insertion of the needle). Additionally, as the needle is at least partially inserted into the body toward the target area and placed, a projected trajectory of the distal tip of the needle to the target area when the needle is advanced distally from the retracted position may be determined based on the position and/or orientation of the distal tip of the needle determined by the position sensing system. A graphical user interface overlaying the position and/or orientation of the distal tip of the needle and the projected trajectory on an image of the target area may be generated and provided for display to guide an operator of the medical device.

In some examples, an ultrasound probe of the system performing the ultrasound imaging may include another device of the position sensing system attached thereto for determining a position and/or orientation of the distal tip of the needle relative to the ultrasound imaging plane. Accordingly, the projected trajectory of the distal tip of the needle to the target area when the needle is advanced distally from the retracted position may also be determined relative to the ultrasound imaging plane.

FIG. 1A depicts a block diagram of an exemplary system 100 for performing an EM-navigated medical procedure. System 100 may include a medical device 102, an imaging system 104 to visually guide insertion and placement of medical device 102 in a patient's body, and a position sensing system 106 for determining a position and/or orientation of medical device 102 within the patient's body. Position sensing system 106 may incorporate any of the features described in U.S. Pat. No. 10,782,114, issued on Sep. 22, 2020, the entirety of which is incorporated herein by reference. Position sensing system 106 may be an EM-based tracking system that includes one or more transmitter devices 108 for generating an electromagnetic field, one or more receiver devices 109 for detecting the electromagnetic field generated, and a controller 107 communicatively coupled to transmitter devices 108 and receiver devices 109, where the position and/or orientation determinations may be based on a strength of the field detected by receiver devices 109, as described in more detail below.

Each of medical device 102 and imaging system 104 may be communicatively coupled to position sensing system 106. Additionally, medical device 102 and/or imaging system 104 may include components of position sensing system 106, such as transmitter devices 108 and/or receiver devices 109, integrated therein. System 100 may further include a separate computing device 110 configured to enable an operator (e.g., a physician) to interact with other systems, such as imaging system 104 and/or position sensing system 106, to generate graphical user interface visualizations for display to the operator. FIG. 1B depicts exemplary components of medical device 102, imaging system 104, and position sensing system 106.

Referring concurrently to FIGS. 1A and 1B, medical device 102 may be a biopsy device including a needle 112 for insertion into a patient's body to obtain a sample of target tissue, where needle 112 extends distally from a handle 114 by which the operator holds or grips medical device 102. Imaging system 104 may be an ultrasound imaging system that includes an imaging console 116 and a probe 118. The ultrasound imaging system may be a two-dimensional (2D) ultrasound imaging system or a three-dimensional (3D) ultrasound imaging system. Once probe 118 is placed near an anatomical structure to be imaged, probe 118 may emit sound waves into the patient's body and receive sound waves that are reflected back. Probe 118 may generate electric signals based on the reflected sound waves that are transmitted to a processing unit of imaging console 116 to generate 2D or 3D images in one or more 2D ultrasound imaging planes for presentation via a display of imaging console 116.

In some examples, the medical procedure may be a prostate biopsy procedure, such as a transperineal biopsy procedure. In the prostate biopsy procedure, probe 118 may be a transrectal ultrasound probe placed in the patient's rectum to provide a 2D imaging plane pointed upwards to image the prostate. Medical device 102 may be a biopsy device with needle 112 that is inserted into the patient through the perineum and into the prostate using the guidance from the ultrasound imaging. Initially, needle 112 of medical device 102 may be in a retracted position when inserted into the patient. For example, at least a portion of needle 112 may be retracted into handle 114 utilizing first and second cocking mechanisms. When a target area (e.g., the prostate) is reached, the medical device 102 may be actuated via handle 114 to cause needle 112 to advance distally from the retracted position to obtain a core biopsy sample of prostate tissue. For example, the first and second cocking mechanisms may be released, causing the needle to advance distally from the retracted position.

The ultrasound imaging plane may be displaced from needle 112 due to the different entry points of probe 118 and needle 112, so it may be difficult for the operator to visualize needle 112 within the ultrasound images until needle 112 is in the imaging plane (e.g., is on-plane) and probe 118 is rotated to a particular position to locate needle 112. Also, in many instances, the operator may be trying to navigate needle 112 at a slight angle to the ultrasound imaging plane, and, as a result, may not be able to see the tip of needle 112. Resultantly, the operator may not be able to predict a trajectory of the distal tip of needle 112 as it is advanced from the retracted position when medical device 102 is actuated. Additionally, as needle 112 embeds into the tissue, needle 112 may bend adding further complexity to the trajectory prediction. If needle 112 follows a different trajectory than predicted when it is advanced from the retracted position, needle 112 may potentially pierce unintended anatomy, such as the rectal wall, urethra, seminal vesicles, and/or blood vessels, which may lead to complications for the patient.

Therefore, to overcome these challenges, position sensing system 106 may be implemented by system 100 to determine a position and/or orientation of needle 112. As previously discussed, position sensing system 106 may include transmitter devices 108 for generating an electromagnetic field and receiver devices 109 for detecting the electromagnetic field generated. In one example aspect, transmitter device 108 may be an external device 120, and receiver devices 109 may include at least an EM sensor disposed in needle 112 of medical device 102 (not shown in this figure and referred to hereinafter as a needle EM sensor) to enable a position and/or orientation of the distal end of needle 112 to be tracked. Additionally, receiver devices 109 may also include a probe EM sensor 122 that is attachable to and detachable from probe 118 to facilitate tracking of a position and/or orientation of the distal tip of needle 112 relative to the ultrasound imaging plane such that the position and/or orientation of the needle 112 may be displayed in the imaging plane. Further, an EM sensor may be disposed in handle 114 of medical device 102 (not shown in this figure and referred to hereinafter as a handle EM sensor). The handle EM sensor may be used to determine a state of medical device 102 (e.g., whether medical device 102 is in a fully cocked state), as described in greater detail below, based on a distance between a fixed point in handle 114 and the needle EM sensor disposed in needle 112. Additionally, or alternatively, the handle EM sensor may be used to measure a second axis to provide six degrees of freedom rather than five degrees of freedom. Resultantly, a computer-generated visualization of an orientation (e.g., in addition to position) of a tip of needle 112 and/or an angular position of handle 114 may be enabled. In another exemplary aspect, transmitter devices 108 generating the magnetic field(s) may include the needle EM sensor, probe EM sensor 122, and/or the handle EM sensor, and receiver device 109 detecting the magnetic field(s) may include external device 120.

Transmitter devices 108 may each include elements to generate a magnetic field. For example, transmitter device 108 may include one or more coils (e.g., solenoids) and one or more circuitry element(s) that transmit current through the coil(s). The coil(s) may thus generate a magnetic field.

Receiver devices 109 may each include one or more magnetic field sensors. Magnetic field sensors may include, for example, magneto-resistive elements, such as TMR elements, anisotropic-magneto-resistive sensing elements, giant magneto-resistive sensing elements, hall-effect sensing elements, colossal magneto-resistive sensing elements, extraordinary magneto-resistive sensing elements, or semi-conductor magneto-resistive elements. Additionally or alternatively, magnetic field sensors may include one or more inductive sensors (e.g., inductive coil sensors), planar coil sensors, spin Hall sensing elements (or other Hall sensing elements), or magnetic gradiometer(s). Magnetic field sensors of receiver devices 109 may have any properties of magnetic field sensors (including, e.g., TMR sensors) known in the art. For example, the magnetic field sensors may include a fixed layer, a tunnel layer, and a free layer. A resistance may change when the free layer is aligned with the fixed layer.

In some examples, at least a portion of receiver devices 109, such as probe EM sensor 122 and/or the handle EM sensor, may have magnetic field sensors arranged in a dual-axis, six-degree-of-freedom arrangement to enable measurements of x, y, z, roll, pitch, and yaw. For example, these portions of receiver devices 109 may include three magnetic field sensors arranged in a dual-axis, six-degree-of-freedom arrangement to enable a positioning of imaging plane to be determined in three dimensions based on the measurements of x, y, z, roll, pitch, and yaw. In such an arrangement, two of three magnetic field sensors may be oriented such that their primary sensing direction is aligned with (approximately parallel to) a longitudinal axis of a respective device in which they are integrated, respectively. A full-Wheatstone bridge configuration may be utilized by the two magnetic field sensors. The third magnetic field sensor may be arranged such that its primary sensing direction is transverse (e.g., approximately orthogonal/perpendicular) to the longitudinal axis. A half-Wheatstone bridge configuration may be utilized by the third magnetic field sensor. The Wheatstone bridges may have any characteristics of Wheatstone bridges known in the art.

Position sensing system 106 may have other configurations within the scope of the disclosure. For example, a tri-axis configuration may be utilized for magnetic field sensors of receiver devices 109, in which each of three magnetic field sensors is arranged so that its primary sensing direction is aligned with a different axis (e.g., the primary sensing directions of magnetic field sensors are aligned orthogonally to one another). For example, a first magnetic field sensor may have a primary sensing direction of the X-axis, a second magnetic field sensor may have a primary sensing direction of the Y-axis, and a third magnetic field sensor may have a primary sensing direction of the Z-axis. In such a tri-axis configuration, each of the magnetic field sensors, may utilize a half-Wheatstone bridge configuration. In another example, only two magnetic field sensors may be utilized by receiver device 109 to measure six degrees of freedom, with each of the two magnetic field sensors having a half-Wheatstone bridge configuration (or a full Wheatstone bridge configuration). In a further example, two magnetic field sensors could be used to measure five degrees of freedom. In such an example, position sensing system 106 may be unable to measure roll. In an additional example, a single magnetic field sensor may be implemented by receiver devices 109 and use a half Wheatstone bridge to measure five degrees of freedom. The needle EM sensor may be arranged in either five degree-of-freedom arrangement (e.g., as it is not necessary to determine orientation of needle 112 around its axis) or a dual-axis, six-degree-of-freedom arrangement.

Controller 107 may be communicatively coupled to transmitter devices 108 and receiver devices 109. For example, controller 107 may be communicatively coupled to external device 120, the needle EM sensor, probe EM sensor 122, and/or the handle EM sensor. Controller 107 may be coupled to the needle EM sensor indirectly via an external cable 124 extending from medical device 102. Controller 107 may be coupled to probe EM sensor 122 directly via an external cable 126 extending from probe EM sensor 122. Controller 107 may transmit signals to transmitter devices 108 to cause transmitter devices 108 to initiate generation of the magnetic field, as well as subsequently pause, stop, and/or restart generation of the magnetic field. Additionally, controller 107 may receive signals from receiver devices 109, the signals indicating a strength of (e.g., a voltage induced by) the magnetic field that is detected by receiver devices 109. A position and/or orientation of a distal tip of needle 112 may be determined based on the signals, where, in some examples, the position and/or orientation is relative to the ultrasound imaging plane.

In the embodiment where receiver devices 109 include the needle EM sensor, probe EM sensor 122, and/or the handle EM sensor, controller 107 may computationally determine a position and/or orientation of a distal tip of needle 112 of medical device 102 based on received signals from the needle EM sensor that indicate a voltage induced by the magnetic field generated by external device 120 as detected by the needle EM sensor. Additionally, controller 107 may computationally determine a position and/or orientation of a distal tip of needle 112 of medical device 102 relative to the ultrasound imaging plane based on received signals from both the needle EM sensor and probe EM sensor 122 that each indicate a voltage induced by the magnetic field generated by external device 120 as detected by the respective EM sensor. Further, based on signals received from the handle EM sensor that measure a second axis, controller 107 may determine the orientation (e.g., in addition to position) of the tip of needle 112, as well as an angular position of handle 114.

In the embodiment where receiver device 109 includes external device 120, controller 107 may computationally determine a position and/or orientation of a distal tip of needle 112 based on the received signals from external device 120 indicating a voltage induced by the magnetic field generated by at least the needle EM sensor as detected by external device 120. Additionally, if probe EM sensor 122 is also a transmitter device 108, controller 107 may computationally determine a position and/or orientation of a distal tip of needle 112 relative to the ultrasound imaging plane based on the received signals from external device 120 indicating a voltage induced by the magnetic field generated by each of the needle EM sensor and probe EM sensor 122 as detected by external device 120.

Separate computing device 110 may communicate with one or more of the other components of system 100 across electronic network 130, including imaging system 104 and/or position sensing system 106, to receive information. For example, computing device 110 may be communicatively coupled to imaging console 116 of imaging system 104 to receive images captured in the ultrasound imaging plane by imaging system 104. Additionally, computing device 110 may be communicatively coupled to controller 107 of position sensing system 106 to receive the positions and/or orientations of needle 112, including the distal tip thereof. In some examples, the received positions and/or orientations of needle 112 may be relative to the imaging plane from controller 107. In further examples, computing device 110 may receive signals via controller 107 that indicate medical device 102 is in a fully cocked state (e.g., needle is retracted) to trigger generation and display of a graphical user interface (GUI) that includes at least a projected needle trajectory for needle 112 overlaid on an image of the target area for biopsy received from imaging system 104.

Computing device 110 may be a computer system such as, for example, a desktop computer, a laptop computer, a tablet, a smart cellular phone, a smart watch or other electronic wearable, etc. In some embodiments, computing device 110 may include one or more electronic application(s), e.g., a program, plugin, browser extension, etc., installed on a memory of computing device 110. The applications may be locally installed and/or web-based accessible via a browser of computing device 110. Additionally, one or more components of computing device 110, such as one of the applications, may generate, or may cause to be generated, one or more GUIs based on instructions/information stored in the memory, instructions/information received from the other systems in the system 100, and/or the like and may cause the GUIs to be displayed via a display of the computing device 110. The GUIs may be, e.g., mobile application interfaces or browser user interfaces and may include text, input text boxes, selection controls, and/or the like. The display may include a touch screen or a display with other input systems (e.g., a mouse, keyboard, etc.) for the operator of computing device 110 to control the functions of computing device 110.

As one example, an application of computing device 110 may utilize the images received from imaging system 104 and the positions and/or orientations of needle 112 relative to the imaging plane received from controller 107 as input to generate a GUI for display on the computing device 110. The GUI may show the position and orientation of the needle 112, including the distal tip thereof, within the imaging plane, as well as a projected three-dimensional trajectory of the needle 112 when it is advanced from the retracted position. The trajectory may be computationally determined based, at least in part, on the position and orientation of a distal tip the needle 112. The GUI may be iteratively updated based on new information received from imaging system 104 and position sensing system 106 (e.g., based on new images and position/orientation information) as the operator further inserts medical device 102 in the patient's body towards the target area for placement and actuates medical device 102 to obtain a core biopsy sample.

Network 130 over which the one or more components of system 100 communicate may include one or more wired and/or wireless networks, such as a wide area network ("WAN"), a local area network ("LAN"), personal area network ("PAN"), a cellular network (e.g., a 3G network, a 4G network, a 5G network, etc.) or the like. In one non-limiting, illustrative example, the components of system 100 may communicate and/or connect to network 130 over universal serial bus (USB) or other similar local, low latency connection or direct wireless protocol. In some embodiments, network 130 includes the Internet, and information and data provided between various systems occurs online.

"Online" may mean connecting to or accessing source data or information from a location remote from other devices or networks coupled to the Internet. Alternatively, "online" may refer to connecting or accessing an electronic network (wired or wireless) via a mobile communications network or device. The Internet is a worldwide system of computer networks—a network of networks in which a party at one computer or other device connected to the network can obtain information from any other computer and communicate with parties of other computers or devices. Computing device 110 and one or more of imaging system 104 and position sensing system 106 may be connected via network 130, using one or more standard communication protocols. Computing device 110 and one or more of imaging system 104 and position sensing system 106 transmit and receive communications from each other across network 130, as discussed in more detail below.

Although depicted as separate components in FIGS. 1A and 1B, it should be understood that a component or portion of a component in system 100 may, in some embodiments, be integrated with or incorporated into one or more other components. For example, rather than being a separate computing device 110, computing device 110 may be integrated with imaging system 104 (e.g., the application may be executed by processing unit of ultrasound imaging console 116 and the GUIs displayed via display of ultrasound imaging console 116), position sensing system 106, or the like. In some embodiments, operations or aspects of one or more of the components discussed above may be distributed amongst one or more other components. Any suitable arrangement and/or integration of the various systems and devices of the system 100 may be used.

While the specific examples included throughout the present disclosure involve a biopsy procedure using medical device 102, it should be understood that techniques according to this disclosure may be adapted to other types of medical procedures, such as brachytherapy procedures for placing seeds, ribbons or capsules containing radiation source in a treatment area of patient's body and/or a fiducial marker placement procedure for placing fiducial markers in a target area of patient's body. For example, the techniques may be adapted to any medical procedure for which a physician utilizes a distal tip of a medical device to pierce/extract or leave behind matter at a particular location within the patient's body. It should also be understood that the examples above are illustrative only. The techniques and technologies of this disclosure may be adapted to any suitable activity.

Figures 2A, 2B, 2C:
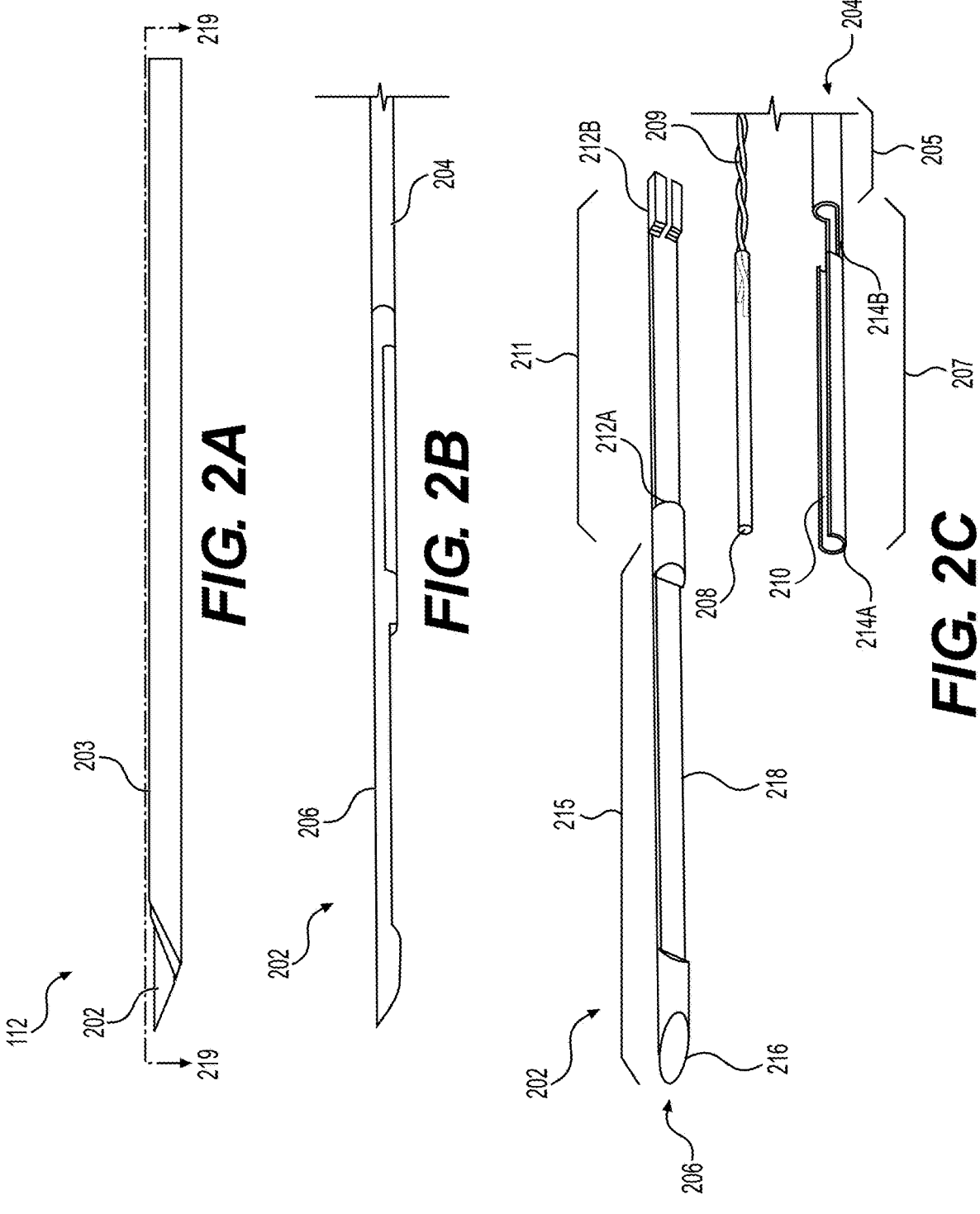
FIGS. 2A-2F depict an exemplary needle of the medical device of FIGS. 1A and 1B.

FIGS. 2A-2F depict one example configuration of needle 112 of medical device 102 described above with reference to FIGS. 1A and 1B. FIG. 2A depicts a side view perspective of a first configuration of needle 112. Needle 112 may include a concentrically arranged core 202 and sheath 203, the core 202 being disposed within sheath 203. A proximal end of needle 112 may extend into handle 114 (not shown). Core 202 and sheath 203 may be independently retractable to a given extent into handle 114. As described in more detail below with respect to FIGS. 3A-5C, core 202 and sheath 203 may be in a neutral position (e.g., are not retracted) when medical device 102 is in neutral state, sheath 203 may be in a retracted position when medical device 102 is in a partially cocked and fully cocked state, core 202 is not retracted when medical device 102 is in a partially cocked state, and core 202 may be in a retracted position when medical device 102 is in the fully cocked state.

In the first configuration, core 202 is disposed within sheath, where only a distalmost portion of core 202 may extend past sheath 203. Core 202 may be positioned relative to sheath 203 in the first configuration when medical device 102 is in the neutral state where both core 202 and sheath 203 are in neutral positions within handle 114, as described with respect to FIGS. 3A-3D, or when medical device 102 is in a fully cocked state where both core 202 and sheath 203 are in retracted positions within handle 114, as described with respect to FIGS. 5A-5C.

At least a distal portion of needle 112 may be inserted into a body of a patient toward a target area comprising target tissue for biopsy while medical device 102 in in the fully cocked state. When medical device 102 is actuated by an operator, core 202 may be advanced distally from the retracted position to the neutral position to pierce and embed into target tissue. Sheath 203 may then be subsequently advanced distally from the retracted position to the neutral position to sever a sample from the tissue.

FIGS. 2B and 2C depict an exemplary core 202 of needle 112. FIG. 2B depicts core 202 in an assembled configuration. FIG. 2C depicts core 202 in a disassembled configuration. Referring concurrently to FIGS. 2B and 2C, core 202 may include a proximal portion 204 and a distal portion 206 distinct from but coupleable to proximal portion 204.

A proximal end 205 of proximal portion 204 of core 202 may extend distally from handle 114 (not shown). A distal end 207 of proximal portion 204 of core 202 may be structurally arranged to receive a needle EM sensor 208. For example, distal end 207 of proximal portion 204 may comprise an open, concave cavity 210 for receiving needle EM sensor 208. Additionally, although proximal end 205 of proximal portion 204 may be fully enclosed, proximal end 205 may be hollow (like a tube) to enable wires 209 of needle EM sensor 208 to be received in and directed through proximal portion 204 and into handle 114.

In some examples, needle EM sensor 208 may be a receiver device 109 of position sensing system 106 configured to detect a magnetic field generated by a transmitter device 108, such as the external device 120 described above with reference FIGS. 1A and 1B. As part of the detection, needle EM sensor 208 may measure a strength of (e.g., a voltage induced by) the magnetic field and provide the measure as a signal to controller 107 for processing to determine the position and/or orientation of the needle 112, and particularly the distal tip of needle 112 (e.g., a distal tip 216 of the core 202). In other examples, needle EM sensor 208 may be a transmitter device 108 of position sensing system 106 configured to generate a magnetic field that is detected by a receiver device 109, such as one or more magnetic field sensors arranged in external device 120, whereby receiver device 109 detects and provides the measure as a signal to the controller 107 for processing.

A proximal end 211 of distal portion 206 of core 202 may be arranged to mate with distal end 207 of proximal portion 204 to couple distal portion 206 and proximal portion 204 with needle EM sensor 208 enclosed therein. That is, a cavity in which needle EM sensor 208 is arranged (and of which cavity 210 forms a part of) may be defined between proximal end 211 of distal portion 206 and distal end 207 of proximal portion 204. For example, an interior surface of proximal end 211 of distal portion 206 may include a first interlocking feature 212A and a second interlocking feature 212B, collectively interlocking features 212. First interlocking feature 212A and second interlocking feature 212B may correspond to a first structural feature 214A and a second structural feature 214B, collectively structural features 214, of distal end 207 of proximal portion 204 to connect or interlock distal portion 206 and proximal portion 204 to form a coupled, assembled configuration of core 202, as shown in FIG. 2B. Coupling of proximal portion 204 and distal portion 206, may be further reinforced based on an arrangement of core 202 within sheath 203 and mechanical limitations placed on sheath retraction and core extension, as shown in and described with respect to FIG. 2D.

Interlocking features 212 may also be adapted to maintain a location and position of needle EM sensor 208 when mated with structural features 214 of distal end 207 of proximal portion 204. For example, needle EM sensor 208 may be constrained to a known location and position between interlocking features 212 within the cavity (of which cavity 210 forms a part of) defined between proximal end 211 of distal portion 206 and distal end 207 of proximal portion 204. Optionally, as core 202 is being manufactured, needle EM sensor 208 may be at least temporarily adhered to the interior surface of proximal end 211 of distal portion 206 at the known location and position between interlocking features 212 to facilitate the handling thereof.

The known location and position of needle EM sensor 208 may be a known distance and position relative to the distal tip of needle 112 (e.g., distal tip 216 of core 202). The known distance and position of needle EM sensor 208 relative to the tip of needle 112 may improve an accuracy of the position and/or orientation determinations performed by position sensing system 106. Additionally, based on the location and position of needle EM sensor 208 being within a distal portion of needle 112 itself, any flex or bend of needle 112 as it enters through tissue, for example, may be accounted for as part of the position and/or orientation determinations performed by position sensing system 106. That is, needle 112 is not assumed to be rigid. Further, because the location and position of needle EM sensor 208 is the same across needles 112, there is no need to calibrate each needle EM sensor 208 during manufacturing.

Distal end 215 of distal portion 206 of core 202 may include distal tip 216 and a sample notch 218. Distal tip 216 may pierce and embed into target tissue when core 202 is advanced distally from the retracted position to the neutral position. Sample notch 218 may capture (e.g., hold) a sample of target tissue when sheath 203 is subsequently advanced distally from the retracted position to the neutral position to sever the sample from the target tissue.

Figures 2D, 2E, 2F:
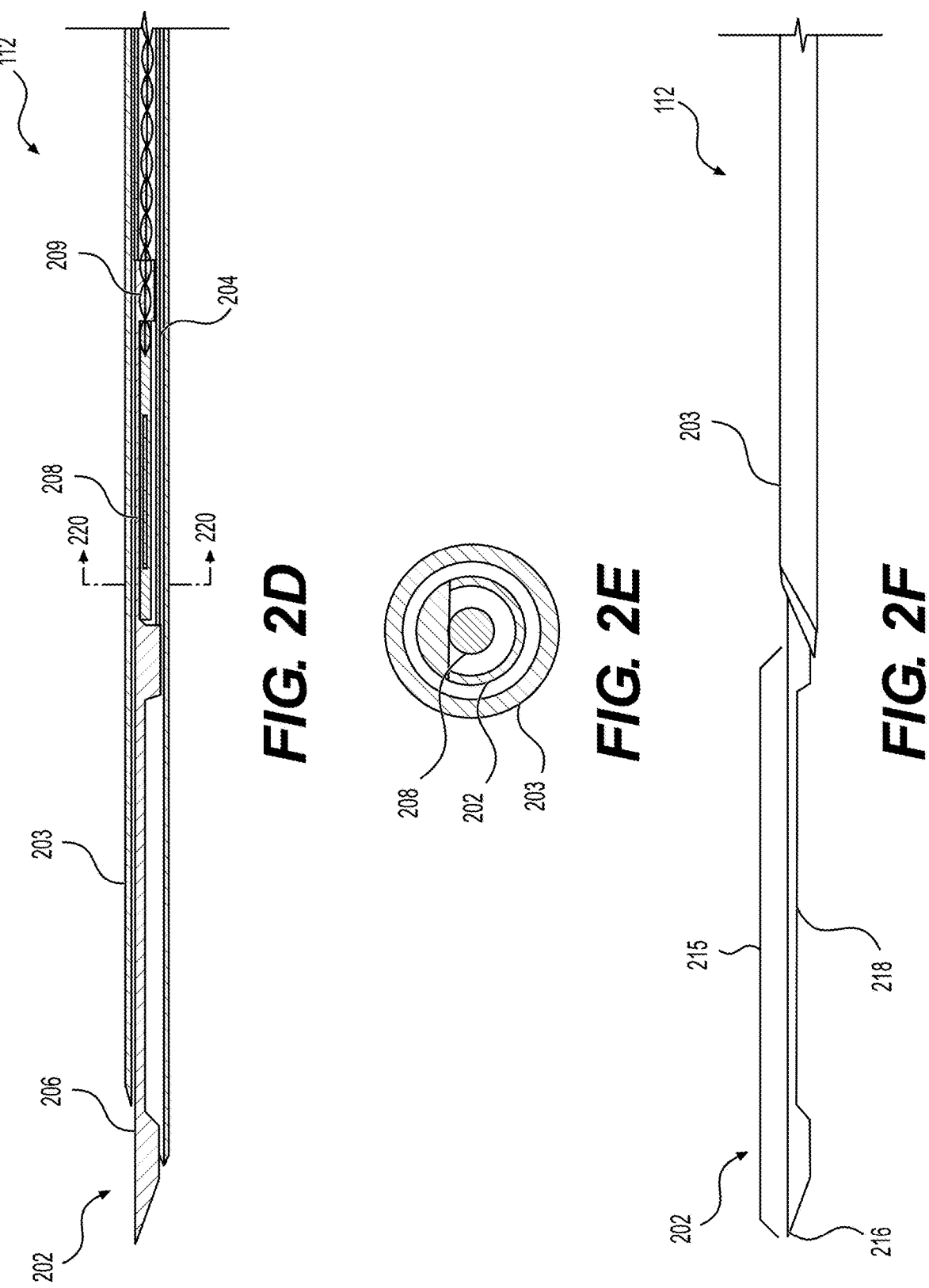

FIG. 2D depicts a cross-section view of needle 112 in the first configuration, taken along line 219 in FIG. 2A, showing an exemplary interior configuration of needle 112 where core 202 is in an assembled configuration having a needle EM sensor 208 arranged in the cavity defined by coupled proximal portion 204 and distal portion 206, and core 202 is disposed within sheath 203. FIG. 2E depicts a complete cross-section view of needle 112 in the first configuration taken at the point along line 220 in FIG. 2D. As shown, an outer diameter of core 202 may be less than an outer diameter and an inner diameter of sheath 203, causing an annular space to be formed between the outer diameter of core 202 and the inner diameter of sheath 203. The annular space may enable sheath 203 and core 202 to retract and advance independently without creating friction. As one non-limiting example, an outer diameter and inner diameter of sheath 203 may be approximately 0.063 inches and approximately 0.051 inches, respectively, and an outer diameter of core 202 may be approximately 0.040 inches. An outer diameter of needle EM sensor 208 may be less than an inner diameter of core 202 where distal end 207 of proximal portion 204 and proximal end 211 of distal portion

206 couple together. Continuing the above non-limiting example, an outer diameter of needle EM sensor 208 may be approximately 0.018 inches.

FIG. 2F depicts a side view perspective of needle 112 in a second configuration. Core 202 may be positioned relative to sheath 203 in the second configuration when medical device 102 is in a partially cocked state prior to medical device 102 actuation, where sheath 203 is in a retracted position and core 202 is in an initial neutral position. Core 202 may also be positioned relative to sheath 203 in the second configuration after medical device 102 has been actuated to capture the target tissue (e.g., after core 202 and sheath 203 have advanced distally from retracted positions to initial neutral position), medical device 102 has been removed from the body, and sheath 203 is returned to the retracted position to release the sample of target tissue from sample notch 218.

An extent of proximal retraction of sheath 203 relative to core 202 may be mechanically limited. For example, and as shown in the second configuration, sheath 203 may not be proximally retracted past distal end 215 of distal portion 206 of core 202. Resultantly, in any given state of medical device 102, the coupled proximal end 211 of distal portion 206 and distal end 207 of proximal portion 204 remain disposed within sheath 203, which reinforces the coupling thereof.

While in FIGS. 2A-2F core 202 of needle 112 has been described as being comprised of two distinct portions 204, 206 coupled to one another to enclose needle EM sensor 208, other configurations of core 202 and needle EM sensor 208 may be implemented. For example, in one alternative configuration, core 202 may be a unitary, solid core and needle EM sensor 208 may be in the form of a coil wound around an outer diameter of core 202. In some examples, the outer diameter of core 202 may include notches to receive the coil such that the coil is isodiametric with the core 202. Additionally, proximal end of core 202 may include a groove or notch to receive and direct wires of needle EM sensor 208 into handle 114. In another alternative configuration, needle EM sensor 208 may be in the form of a coil wound around an outer diameter of sheath 203. In some examples, the outer diameter of sheath 203 may include notches to receive the coil such that the coil is isodiametric with the sheath 203.

FIGS. 3A-5C depict interactions of needle 112 and handle 114 components of medical device 102 in various device states, including a neutral state, a partially cocked state, and a fully cocked state.

Figures 3A, 3B, 3C:
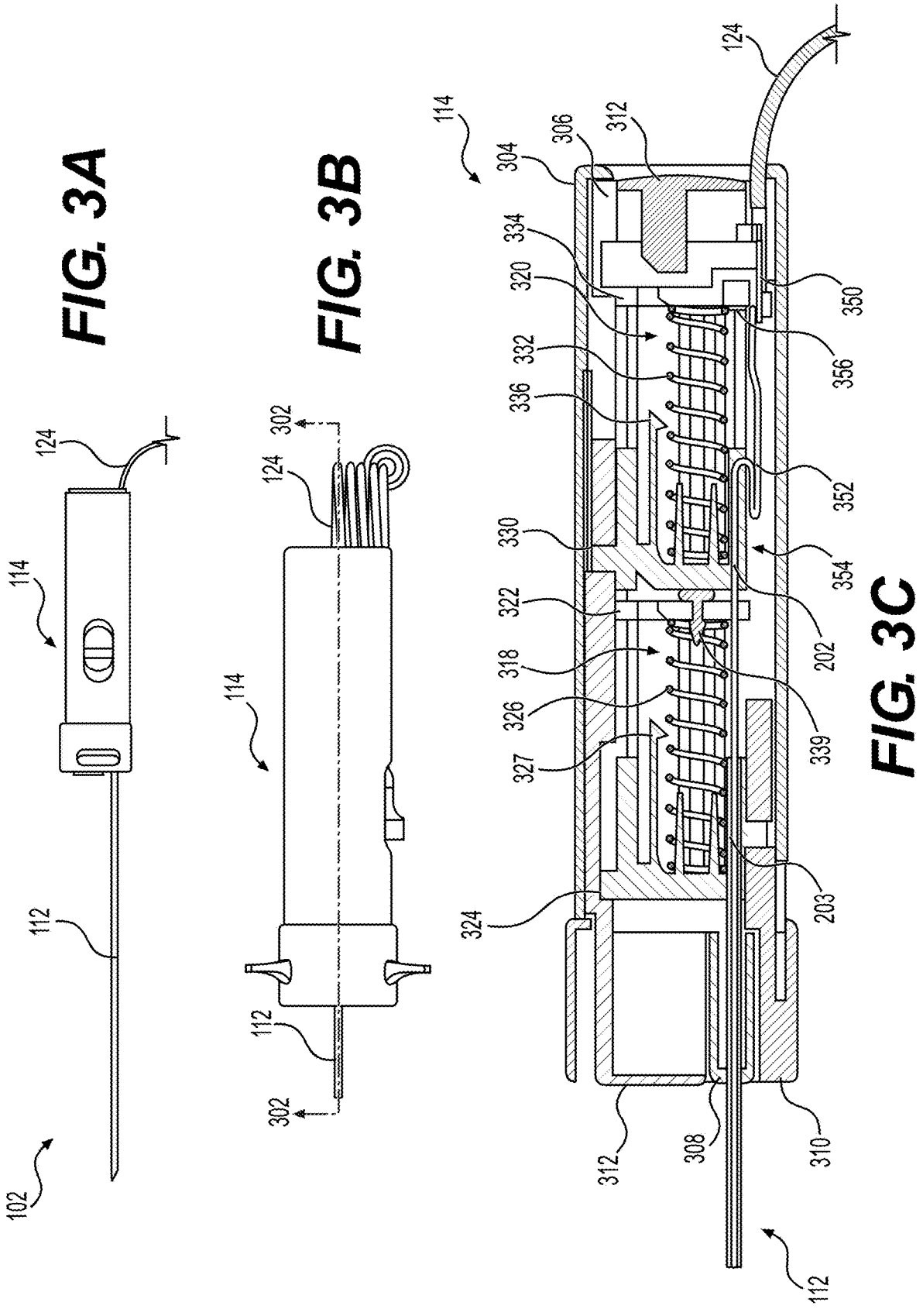
FIGS. 3A-3D depict the medical device of FIGS. 1A and 1B in an exemplary neutral state.

FIGS. 3A-3D depict medical device 102 in a neutral state. FIG. 3A depicts an exterior view of an entirety of medical device 102 in a neutral state. Core 202 and sheath 203 of needle 112 extend distally from handle 114 in the first configuration, where only a distalmost portion of core 202 (e.g., distal tip 216) may extend past sheath 203, as described with reference to FIG. 2A. Core 202 and sheath 203 may be in a neutral position within handle 114. External cable 124 extending from a proximal end of handle 114 may communicatively couple needle EM sensor 208 positioned within core 202 of needle 112 to controller 107 of position sensing system 106.

Figure 3D:
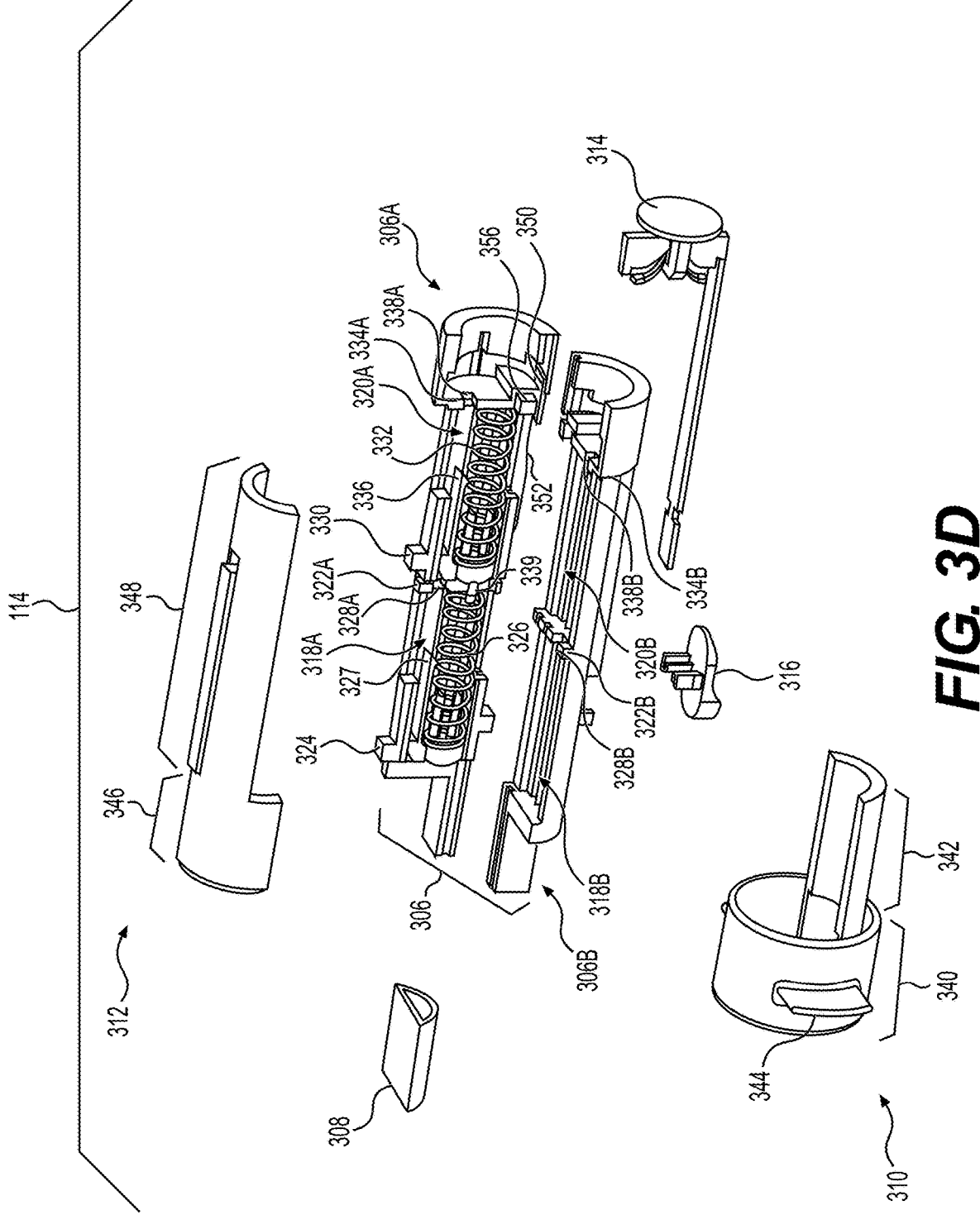

FIG. 3B illustrates another exterior view of medical device 102 in the neutral state where only a proximal portion of needle 112 is shown extending distally from handle 114 and device 102 is rotated about 90 degrees from a position of medical device 102 in FIG. 3A. FIG. 3C is a cross-section view, taken along line 302 in FIG. 3B, to depict interactions of components of handle 114 with one another and with needle 112. FIG. 3D is an exploded view of handle 114 depicted in FIG. 3B with an outer housing 304 of handle 114 removed.

Referring concurrently to FIGS. 3C and 3D, components of handle 114 may include an outer housing 304 that encloses at least portions of a frame 306 supporting first and second cocking mechanisms for independently retracting core 202 and sheath 203 of needle 112 into handle 114, a connector 308 for frame 306, a first cocking actuator 310 associated with a retraction of sheath 203, a second cocking actuator 312 associated with a retraction of core 202, and one or more trigger devices, such as rear trigger device 314 and side trigger device 316, for actuating medical device 102 when fully cocked.

Figures 4A, 4B, 4C:
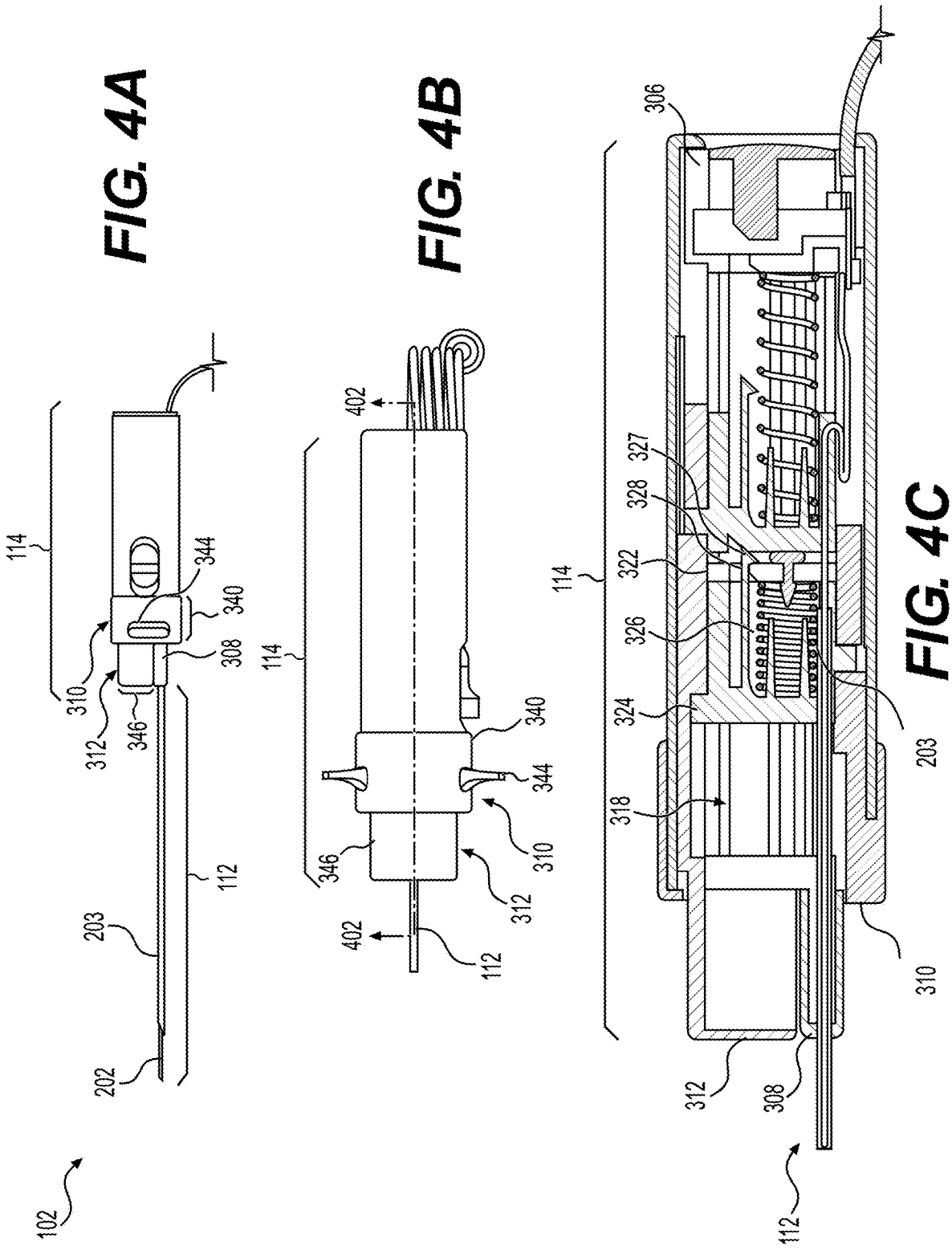
FIGS. 4A-4C depict the medical device of FIGS. 1A and 1B in an exemplary partially cocked state.
Figures 5A, 5B, 5C:
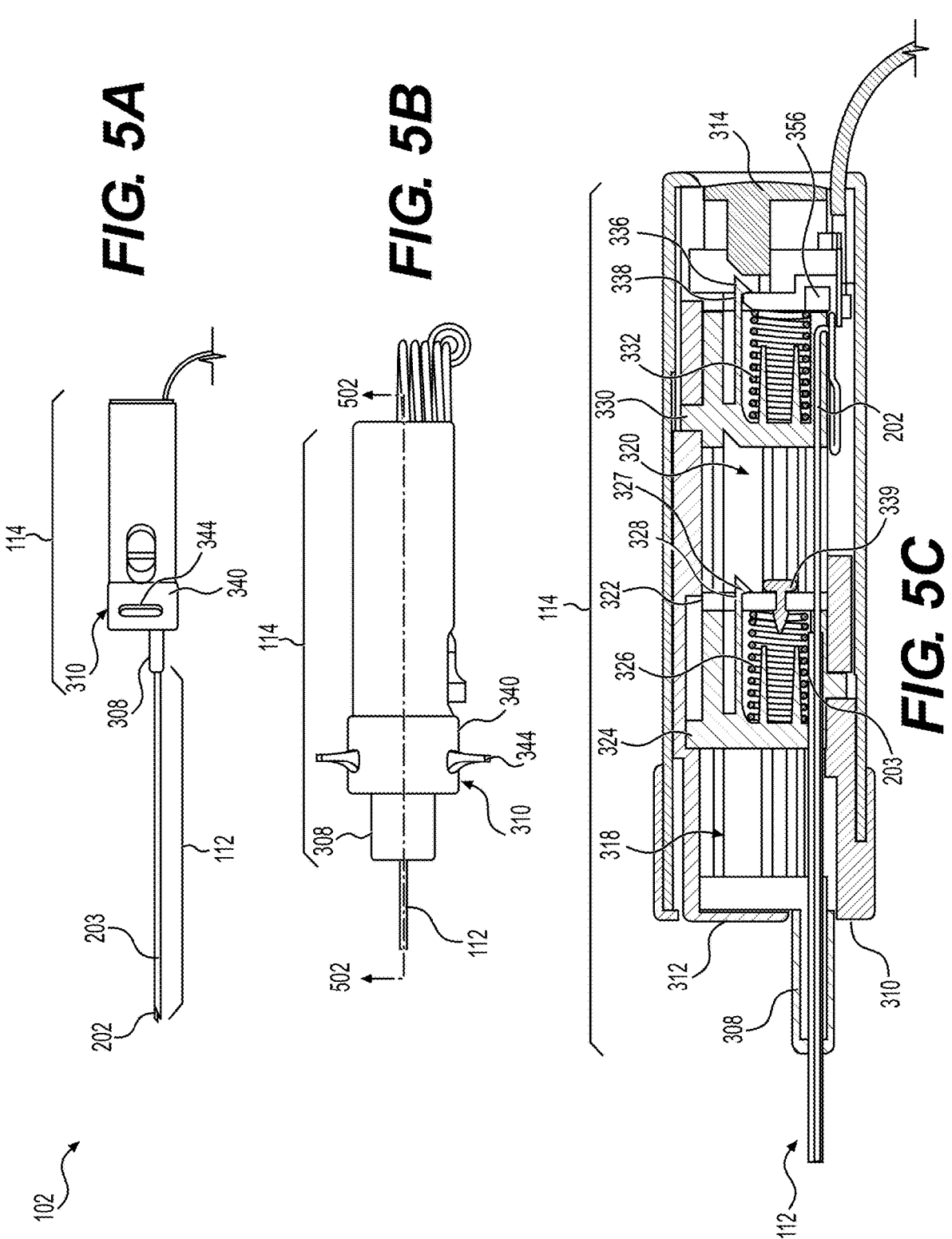
FIGS. 5A-5C depict the medical device of FIGS. 1A and 1B in an exemplary fully cocked state.

Frame 306 may include a first sub-frame 306A and a second sub-frame 306B that are coupled to one another by connector 308 to form frame 306. First sub-frame 306A may include a distal interior chamber 318A and a proximal interior chamber 320A separated by a separator wall 322A. Distal interior chamber 318A may support a first cocking mechanism associated with sheath 203. For example, distal interior chamber 318A may be configured to receive a sheath slider 324 and a sheath spring 326, with sheath spring 326 being interposed between sheath slider 324 and separator wall 322A. Sheath slider 324 may be fixed to a proximal end of sheath 203. A portion of sheath slider 324 may protrude from first sub-frame 306A and connect with first cocking actuator 310 to enable movement of sheath slider 324 to a cocked position to retract sheath 203 when first cocking actuator 310 is actuated. Sheath slider 324 may have a locking feature 327 at a proximal end, and separator wall 322A may include a lock opening 328A configured to receive locking feature 327 of sheath slider 324 when sheath slider 324 is moved to the cocked position based on an actuation of first cocking actuator 310, as shown in FIG. 4C and FIG. 5C.

Proximal interior chamber 320A may support a second cocking mechanism associated with core 202. For example, proximal interior chamber 320A may be configured to receive a core slider 330 and a core spring 332, with core spring 332 being interposed between core slider 330 and an end wall 334A. Core slider 330 may be fixed to a proximal end of core 202. A portion of core slider 330 may protrude from first sub-frame 306A and connect with second cocking actuator 312 to enable movement of core slider 330 to a cocked position to retract core 202 when second cocking actuator 312 is actuated. A proximal end of core slider 330 may have a locking feature 336, and end wall 334A may include a lock opening 338A configured to receive locking feature 336 of core slider 330 when core slider 330 is moved to the cocked position based on an actuation of second cocking actuator 312, as shown in FIG. 5C. The second cocking mechanism may be cocked subsequent to or concurrently with the first cocking mechanism. Medical device 102 may not be actuated by an operator until both first cocking mechanism and second cocking mechanism are cocked.

Second sub-frame 306B may be a mirror image of first sub-frame 306A discussed above to form frame 306. For example, second sub-frame 306B may include a distal interior chamber 318B and a proximal interior chamber 320B separated by a separator wall 322B with a lock opening 328B that is a mirror image of distal interior chamber 318A and proximal interior chamber 320A separated by separator wall 322A with lock opening 328A. Additionally, second sub-frame 306B may include an end wall 334B with a lock opening 338B that is a mirror image of end wall 334A with lock opening 338A of first sub-frame 306A. Resultantly, when first sub-frame 306A and second sub-frame 306B are connected via connector 308, frame 306 comprises distal interior chamber 318 formed from distal interior chambers 318A, 318B, proximal interior chamber 320 formed from proximal interior chambers 320A, 320B, separator wall 322 with lock opening 328 formed by separator walls 322A, 322B with respective lock openings 328A, 328B, and end wall 334 with lock opening 338 formed by end walls 334A, 334B with respective lock openings 338A, 338B.

A stopper 339 may be positioned between distal interior chamber 318 and proximal interior chamber 320 and extend through an opening in separator wall 322. Stopper 339 may be a silicone stopper that the second cocking mechanism collides with after the second cocking mechanism is released from the cocked position based on an actuation of one of trigger devices, such as rear trigger device 314 and/or side trigger device 316. A kinetic force from the collision temporarily compresses stopper 339 to cause release of locking feature 327 of sheath slider 324 from lock opening 328A to allow release of the first cocking mechanism, before stopper 339 rebounds to a position that doesn't inhibit locking feature 327 of sheath slider 324 from again being captured within lock opening 328A a next time the first cocking mechanism is cocked.

First cocking actuator 310 may include an exterior portion 340 accessible by an operator of medical device 102 and an interior portion 342 extending within outer housing 304. Exterior portion 340 may include one or more gripping features 344 to provide the operator a better grip when moving first cocking actuator 310 proximally toward proximal end of handle 114 to transition medical device 102 from the neutral state to a partially cocked state as shown and described with reference to FIGS. 4A-4C. Interior portion 342 may be connected to sheath slider 324 to cause sheath slider 324 to compress sheath spring 326 proximally toward separator wall 322 when exterior portion 340 of first cocking actuator 310 is moved proximally toward proximal end of handle 114. Additionally, exterior portion 340 may be hollow to receive at least a portion of second cocking actuator 312 and connector 308, as discussed below.

Second cocking actuator 312 may include an exterior portion 346 accessible by an operator of medical device 102 and an interior portion 348 extending within outer housing 304. In some examples, exterior portion 346 of second cocking actuator 312 may be disposed within exterior portion 340 of first cocking actuator 310 when medical device 102 is in the neutral state. When exterior portion 340 of first cocking actuator 310 is moved proximally toward proximal end of handle 114 to transition medical device 102 from the neutral state to the partially cocked state, exterior portion 346 may be exposed and readily accessible by the operator. Interior portion 348 may be connected to core slider 330 to cause core slider 330 to compress core spring 332 proximally toward end wall 334 when exterior portion 346 of second cocking actuator 312 is moved proximally toward proximal end of handle 114.

Within handle 114, wires 209 of needle EM sensor 208 may be routed out of proximal portion 204 of core 202 and connected to an interposer board 350. Interposer board 350 may be an electrical interface routing signals from wires 209 to controller 107 of position sensing system 106 via external cable 124 also connected to interposer board 350. Between proximal portion 204 of core 202 and interposer board 350, wires 209 may be contained within an internal cable 352 that provides greater resistance to bending to minimize kinking and mechanical fatigue when core 202 is retracted and advanced.

Additionally, handle 114 may include a service loop compartment 354 (e.g., a hollow cavity) located between frame 306, interior portion 342 of first cocking actuator 310 and outer housing 304. Internal cable 352 may be routed from proximal portion 204 of core 202 through service loop compartment 354 to interposer board 350. Service loop compartment 354 may enable a given length of internal cable 352 to accumulate and form a service loop to provide internal cable 352 freedom of movement or slack (e.g., to prevent tension) as core 202 is retracted and advanced. Additionally, by forming a service loop within dedicated service loop compartment 354, when medical device 102 is fired causing core 202 to advance and thus internal cable 352 to advance therewith, internal cable 352 may smoothly advance without catching on any other component within handle 114.

Figures 7A, 7B, 7C:
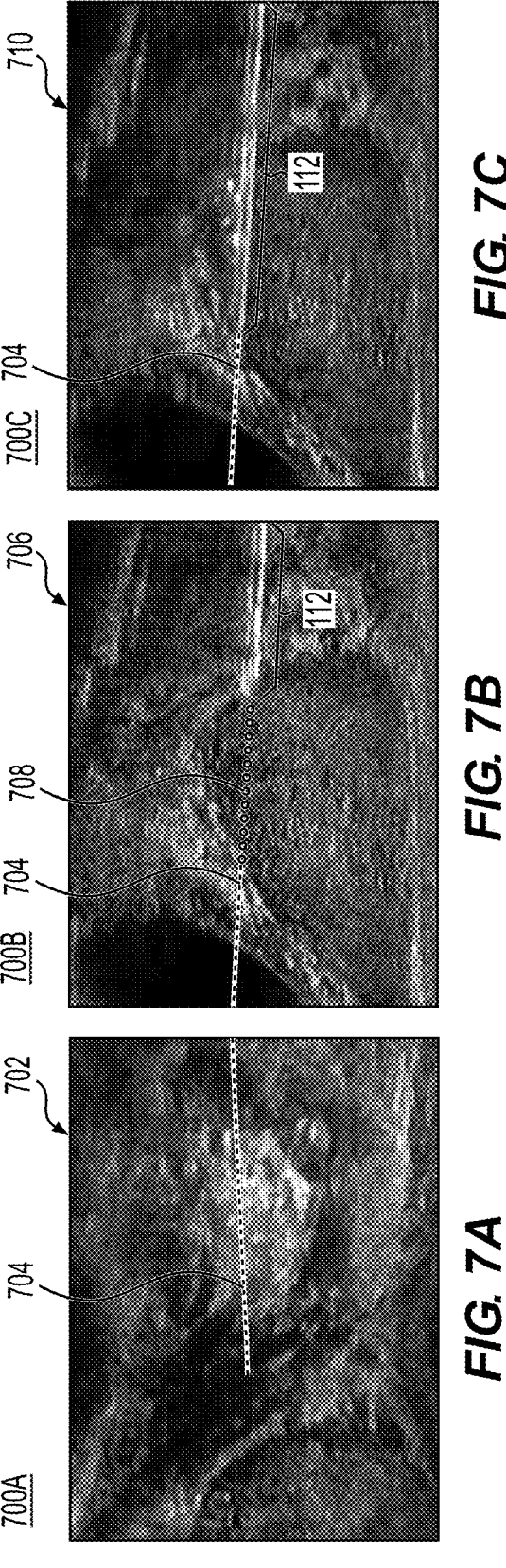
FIGS. 7A-7C depict exemplary graphical user interfaces.

Further, a switch 356 may be directly connected to interposer board 350 (e.g., via soldering) and received within first sub-frame 306A. Switch 356 may be a mechanically actuated electrical switch that is configured to detect when the second cocking mechanism associated with core 202 is cocked, and thus medical device 102 is in a fully cocked state, as shown in FIGS. 5A-C. In some examples, switch 356 may be wired between two erasable programmable read-only memories (EPROMs). Each EPROM may be read as a different device ID. The device ID may be provided as a signal to controller 107 via external cable 124, and controller 107 may forward the signal to computing device 110, where the application executing on computing device 110 may be programed to recognize the different device IDs as either the fully cocked state or non-fully cocked (e.g., neutral or partially cocked) state of medical device 102. In some examples, based on the recognition of the fully cocked state, the application of computing device 110 may utilize the images received from imaging system 104 and the positions and/or orientations of the distal tip of needle 112 relative to the imaging plane received from controller 107 as input to generate a GUI for display on the computing device 110. For example, at least a projected needle trajectory for needle 112 may be overlaid on an image of the target tissue, as shown in FIG. 7A. In other examples, switch 356 and/or any of the alternatives for switch 356 discussed below may be omitted such that at least a projected needle trajectory overlaid on an image of the target tissue is always shown within a GUI (e.g., even if medical device 102 is not fully cocked).

In other examples, switch 356 may be substituted for a different switch that detects when the second cocking mechanism is in the neutral position (e.g., is not cocked). This different switch could be located adjacent to any moving part in handle 114. Additionally, switch 356 may be substituted by a sensor configured to measure the position or proximity of the moving parts of handle 114, including optical, magnetic, capacitive, ultrasonic, or electromagnetic induction sensors. Further, the application executing on computing device 110 may itself detect a change of medical device 102 from neutral state to fully cocked state, or vice-versa, by measuring a velocity of needle EM sensor 208.

FIGS. 4A-4C depict medical device 102 in a partially cocked state. Medical device 102 may be in a partially cocked state when the first cocking mechanism associated with sheath 203 is in a cocked position in distal interior chamber 318 while the second cocking mechanism associated with core 202 is in a neutral position in proximal interior chamber 320. FIG. 4A depicts an exterior view of an entirety of medical device 102 in a partially cocked state. Needle 112 extending distally from handle 114 may be in the second configuration described with reference to FIG. 2F, where distal end 215 of distal portion 206 of core 202 is exposed when sheath 203 is in a retracted position in handle 114. FIG. 4B illustrates another exterior view of medical device 102 in a partially cocked state where only a proximal portion of needle 112 is shown extending distally from handle 114 and device 102 is rotated about 90 degrees from a position of medical device 102 in FIG. 4A. FIG. 4C is a cross-section view, taken along line 402 in FIG. 4B, to depict interactions of components of handle 114 with one another and with needle 112 in the partially cocked state.

Referring concurrently to FIGS. 4A-4C, as an operator of medical device 102 proximally moves exterior portion 340 of first cocking actuator 310 (e.g., using gripping features 344) toward proximal end of handle 114, the portion of sheath slider 324 connected to interior portion 342 of first cocking actuator 310 may move sheath slider 324 and proximal end of sheath 203 connected to sheath slider 324 toward separator wall 322 causing sheath 203 to retract from a neutral position to a retracted position. This movement causes sheath spring 326 to compress and locking feature 327 of sheath slider 324 to enter through lock opening 328 to lock the first cocking mechanism into the cocked position. Proximal movement of exterior portion 340 of first cocking actuator 310 may cause exterior portion 346 of second cocking actuator 312 and connector 308 to be exposed.

FIGS. 5A-5C depict medical device 102 in a fully cocked state. Medical device 102 may be in a fully cocked state when both the first cocking mechanism associated with sheath 203 and the second cocking mechanism associated with core 202 are in a cocked position in the distal interior chamber 318 and proximal interior chamber 320, respectively. FIG. 5A depicts an exterior view of an entirety of medical device 102 in a fully cocked state. Core 202 and sheath 203 of needle 112 extending distally from handle 114 may be in the first configuration, where only a distalmost portion of core 202 (e.g., distal tip 216) may extend past sheath 203, as described with reference to FIG. 2A. Additionally, core 202 and sheath 203 may both be in a retracted position within handle 114 when medical device 102 is in the fully cocked state. FIG. 5B illustrates another exterior view of medical device 102 in the fully cocked state where only a proximal portion of needle 112 is shown extending distally from handle 114 and medical device 102 is rotated about 90 degrees from a position of medical device 102 in FIG. 5A. FIG. 5C is a cross-section view, taken along line 502 in FIG. 5B, to depict interactions of components of handle 114 with one another and with needle 112 in the fully cocked state.

Referring concurrently to FIGS. 5A-5C, subsequent to or concurrently with the operator's movement of exterior portion 340 of first cocking actuator 310 (e.g., using gripping features 344) toward distal end of handle 114 to lock the first cocking mechanism into the cocked position as described with reference to FIGS. 4A-4C, the operator may drive exterior portion 346 of second cocking actuator 312 toward proximal end of handle 114 to lock the second cocking mechanism into the cocked position. Proximal driving of exterior portion 346 of second cocking actuator 312 may result in only connector 308 being exposed as exterior portion 346 of second cocking actuator 312 is now disposed within exterior portion 340 of first cocking actuator 310.

As the operator drives exterior portion 346 of second cocking actuator 312, the portion of core slider 330 connected to interior portion 348 of second cocking actuator 312 may move core slider 330 and proximal end of core 202 connected to core slider 330 toward end wall 334 causing core 202 to retract from a neutral position to a retracted position. This movement causes core spring 332 to compress and locking feature 336 of core slider 330 to enter through lock opening 338 to lock the second cocking mechanism into the cocked position.

In some example aspects, switch 356 may detect the second cocking mechanism in the cocked position and cause signals indicating the fully cocked state of medical device 102 to be provided via interposer board 350 to controller 107 and ultimately to computing device 110 to cause generation and display of GUIs to facilitate use of medical device 102 during the medical procedure. Proximal driving of exterior portion 346 of second cocking actuator 312 may result in only connector 308 being exposed as exterior portion 346 of second cocking actuator 312 is now disposed within exterior portion 340 of first cocking actuator 310.

Once inserted into patient's body and positioned in relation to target tissue using guidance from the GUIs, medical device 102 may be actuated using one of the trigger devices, such as rear trigger device 314. Force from the operator's pressing of rear trigger device 314 may cause release of locking feature 336 of core slider 330 from lock opening 338 to allow release of the second cocking mechanism from the cocked position. Release of the second cocking mechanism advances core 202 of needle 112 distally from the retracted position to pierce into and embed in target tissue. The second cocking mechanism may collide with stopper 339 after the second cocking mechanism is released from the cocked position, where a kinetic force from the collision temporarily compresses stopper 339 to cause release of locking feature 327 of sheath slider 324 from lock opening 328 to allow release of the first cocking mechanism from the cocked position. Release of the first cocking mechanism advances sheath 203 of needle 112 distally from the retracted position to sever a sample of the target tissue that is captured within sample notch 218 of core 202. The operator may then remove medical device 102 from the patient's body. To retrieve the sample of the target tissue captured within sample notch 218, medical device 102 may be returned to a partially cocked state as described with respect to FIGS. 4A-4C.

Although not shown in FIGS. 3A-5C, in some examples, medical device 102 may include a control element (e.g., a switch) that physically limits a length of travel for the first and second cocking mechanism within distal interior chamber 318 and proximal interior chamber 320. The control element allows the operator to adjust the length of travel to correspond to a given biopsy sample length associated with the procedure at hand. Additionally, the control element may be coupled to an electrical switch that may communicate the given biopsy sample length to the application executing on computing device 110. In some examples, where handle 114 includes the handle EM sensor disposed therein, the control element may further be coupled to the handle EM sensor to measure a distance to the needle EM sensor, and thus determine a position of the control element and the length of travel. The GUI generated by application may account for and provide a needle trajectory that reflects the given biopsy sample length.

Additionally, although not shown in FIGS. 3A-5C, handle 114 may also include the handle EM sensor described with reference to FIGS. 1A and 1B.

FIG. 6 depicts an exemplary process 600 to generate a graphical user interface to visualize a position and/or an orientation of medical device 102, and particularly a distal tip of needle 112 of medical device 102. In some examples, process 600 may be performed by computing device 110 based on information received from other components of system 100, such as imaging system 104 and position sensing system 106.

Following insertion of at least a portion of needle 112 of medical device 102 into a patient's body, at step 602, process 600 may include receiving signals from one or more receiver devices 109 that indicate a strength of (e.g., a voltage induced by) a magnetic field generated by one or more transmitter devices 108 as detected by receiver device 109. At least one of the receiver devices 109 or transmitter devices 108 includes an EM sensor positioned within needle 112 (e.g., needle EM sensor 208 positioned in a fixed location within core 202). In one example, the receiver devices 109 may include the needle EM sensor 208 and probe EM sensor 122 (and optionally the handle EM sensor), and transmitter device 108 may include external device 120. In another example, the receiver device 109 may include external device 120, and transmitter devices 108 may include needle EM sensor 208 and probe EM sensor 122 (and optionally the handle EM sensor).

At step 604, process 600 may include determining a position and/or an orientation of a distal tip of needle 112 (e.g., a distal tip 216 of core 202) based on the received signals. In some embodiments, the position and/or orientation of the distal tip may be further determined relative to the ultrasound imaging plane of imaging system 104. For example, by including probe EM sensor 122 as part of position sensing system 106, the signals received may indicate a position and orientation of the distal tip of needle 112 relative to the imaging plane.

At step 606, process 600 may include determining a projected trajectory of the distal tip of needle 112 when medical device 102 is actuated causing needle 112 to advance distally based on the position and/or orientation of the distal tip of needle 112 determined at step 604. In some examples, determining the projected trajectory may be based on the position and/or orientation of the distal tip of needle 112 and a transformation matrix that describes the spatial relation between needle EM sensor 208 and medical device 102. For example, the transformation matrix may include numbers describing a 3D position offset between the distal tip of needle 112 and a magnetic center of needle EM sensor 208, and the 2D (or 3D, if needle EM sensor 208 is a six degree of freedom sensor) rotational offset between the axis of needle 112 with the axis of needle EM sensor 208.

In some examples, the transformation matrix may be determined by a dimensional offset that is incorporated into a design of needle 112, and thus applied to all medical devices 102 including needle 112 of the given design. Additionally or alternatively, a calibration method may be performed on each medical device 102, where medical device 102 and/or a calibration tool are physically moved and tracked in order to take measurements that allow an algorithm to deduce the spatial relation between needle EM sensor 208 and medical device 102. One non-limiting, illustrative calibration method may be a pivot calibration, where medical device 102 is rotated and/or pivoted around the distal tip of needle 112 as the distal tip held in a stationary position.

Additionally, in examples where probe EM sensor 122 is included as part of position sensing system 106, and the signals received from probe EM sensor 122 indicate a position and orientation of the distal tip of needle 112 relative to the imaging plane, the trajectory may be further determined based on a spatial relation between probe 118 and probe EM sensor 122. A similar calibration may be performed to allow an algorithm to deduce the spatial relation between probe EM sensor 122 and probe 118.

At step 608, process 600 may include receiving an image of a target area from imaging system 104. For example, the image may be an ultrasound image captured by imaging system 104 in the imaging plane. The target area may be an area including target tissue from which a sample is to be obtained.

At step 610, process 600 may include generating a graphical user interface (GUI) that overlays the position and/or orientation of the distal tip of needle 112 determined at step 604 and the projected trajectory of the distal tip of needle 112 determined at step 606 on the image received at step 608. At step 612, process 600 may include providing the GUI for display on a display device, such as a display of computing device 110.

Process 600 may be periodically repeated to update the GUI as the operator further inserts medical device 102 in the patient's body towards the target area to place needle 112 and actuates medical device 102 to obtain a core biopsy sample. Also, while process 600 describes generation of GUIs following insertion of needle 112 into the patient's body, additional GUIs may also be generated in advance of the insertion that display a projected needle trajectory depicting an expected path of needle 112 to target area overlaid on an image of the target area to help guide insertion of needle 112. In some examples, at least a portion of the projected needle trajectory may remain displayed on the GUI generated and displayed at steps 610 and 612. Examples GUIs are illustrated and described with respect to FIGS. 7A-7C below.

Accordingly, certain embodiments may generate a graphical user interface to visualize a position and/or orientation of medical device 102. Process 600 described above is provided merely as an example, and may include additional, fewer, different, or differently arranged steps than depicted in FIG. 6.

In this disclosure, various acts may be described as performed or executed by a component from FIGS. 1A and 1B, such as the computing device 110. However, it should be understood that in various embodiments, various components of the exemplary system 100 discussed above may execute instructions or perform acts including the acts discussed above. An act performed by a device may be considered to be performed by a processor, actuator, or the like associated with that device. Further, it should be understood that in various embodiments, various steps may be added, omitted, and/or rearranged in any suitable manner.

FIGS. 7A-C depict exemplary graphical user interfaces generated and displayed during a medical procedure. FIG. 7A depicts an exemplary graphical user interface 700A generated prior to insertion of needle 112. Graphical user interface 700A may include a first ultrasound image 702 of a target area associated with a medical procedure, such as target biopsy area, from imaging system 104. A projected needle trajectory 704 that includes an expected or desired path for needle 112 once inserted into the patient's body may be overlaid on first ultrasound image 702 to guide the operator of medical device 102. For example, visualizing projected needle trajectory 704 may allow the operator to precisely plan placement of needle 112 to reach the target area and minimize unnecessary trauma from repeated punctures with needle 112.

FIG. 7B depicts an exemplary graphical user interface 700B generated using process 600 after insertion of needle 112 and prior to actuation of medical device 102 (e.g., prior to user actuating rear trigger device 314 or side trigger device 316). When needle 112 is inserted into the patient's body, medical device 102 is in a fully cocked state, where both core 202 and sheath 203 of needle 112 are in a retracted position. Graphical user interface 700B may include a second ultrasound image 706 of the target area including a location and orientation of needle 112, including a distal tip thereof, relative to the ultrasound imaging plane as it approaches the target area. Projected needle trajectory 704 may remain overlaid on second ultrasound image 706. Additionally, a biopsy path indicator 708 may be overlaid on second ultrasound image 706. Biopsy path indicator 708 may align with a portion of projected needle trajectory 704, and corresponds to a projected trajectory of needle 112 (e.g., determined at step 606 of process 600) when medical device 102 is actuated causing needle 112 to advance distally from the retracted position (e.g., core 202 followed by sheath 203).

FIG. 7C depicts an exemplary graphical user interface 7000 generated after actuation of medical device 102. When medical device 102 is actuated, needle 112 advances distally from its retracted position to capture a biopsy sample of the target area. Graphical user interface 7000 may include a third ultrasound image 710 of the target area including a location and orientation of needle 112, including the distal tip thereof, relative to the ultrasound imaging plane after needle 112 has advanced distally from the retracted position (e.g., along a path indicated by biopsy path indicator 708). While a portion of projected needle trajectory 704 may remain overlaid on third ultrasound image 710 (e.g., the portion extending beyond the distal tip of needle 112 when actuated), biopsy path indicator 708 may be replaced by needle 112 itself that has advanced distally along the path indicated by biopsy path indicator 708.

Although not shown in FIGS. 7A-7C, various other visual schemes may be employed within GUIs generated using information from imaging system 104 and position sensing system 106. As one example, a location of a distal tip of needle 112 (e.g., distal tip 216 of core 202) may be highlighted or otherwise emphasized with a distinct visual marker such that the operator of medical device 102 can be more easily aware of when the distal tip is not on the image plane. Additionally or alternatively, other visual indicators like color, outlines, or flashing markers may be used to indicate when a position of needle 112 is not on the ultrasound imaging plane to inform the operator that a trajectory of needle 112 will not pass through the tissue cross section currently displayed on the GUI. To further assist the operator, an intersection of needle 112 and trajectory of needle 112 with the ultrasound plane can be highlighted as the operator rotates probe 118 to evaluate the tissue volume. In some examples, a 3D representation of a tip of probe 118, ultrasound imaging plane, and needle 112 may be generated by application of computing device 110 based on information received from imaging system 104 and position sensing system 106. The representation may be displayed to show the operator where needle 112 is relative to the ultrasound imaging plane. Further, application of computing device 110 may compute a 3D reconstruction of the tissue based on images captured by imaging system 104 when the user rotates probe 118, to allow the operator to visualize the entire volume of interest to identify the areas for biopsy and/or check for structures to avoid during the biopsy procedure. The volume of interest may include the volume surrounding a trajectory for needle 112, or an entire area shown in the ultrasound images.

Figure 8:
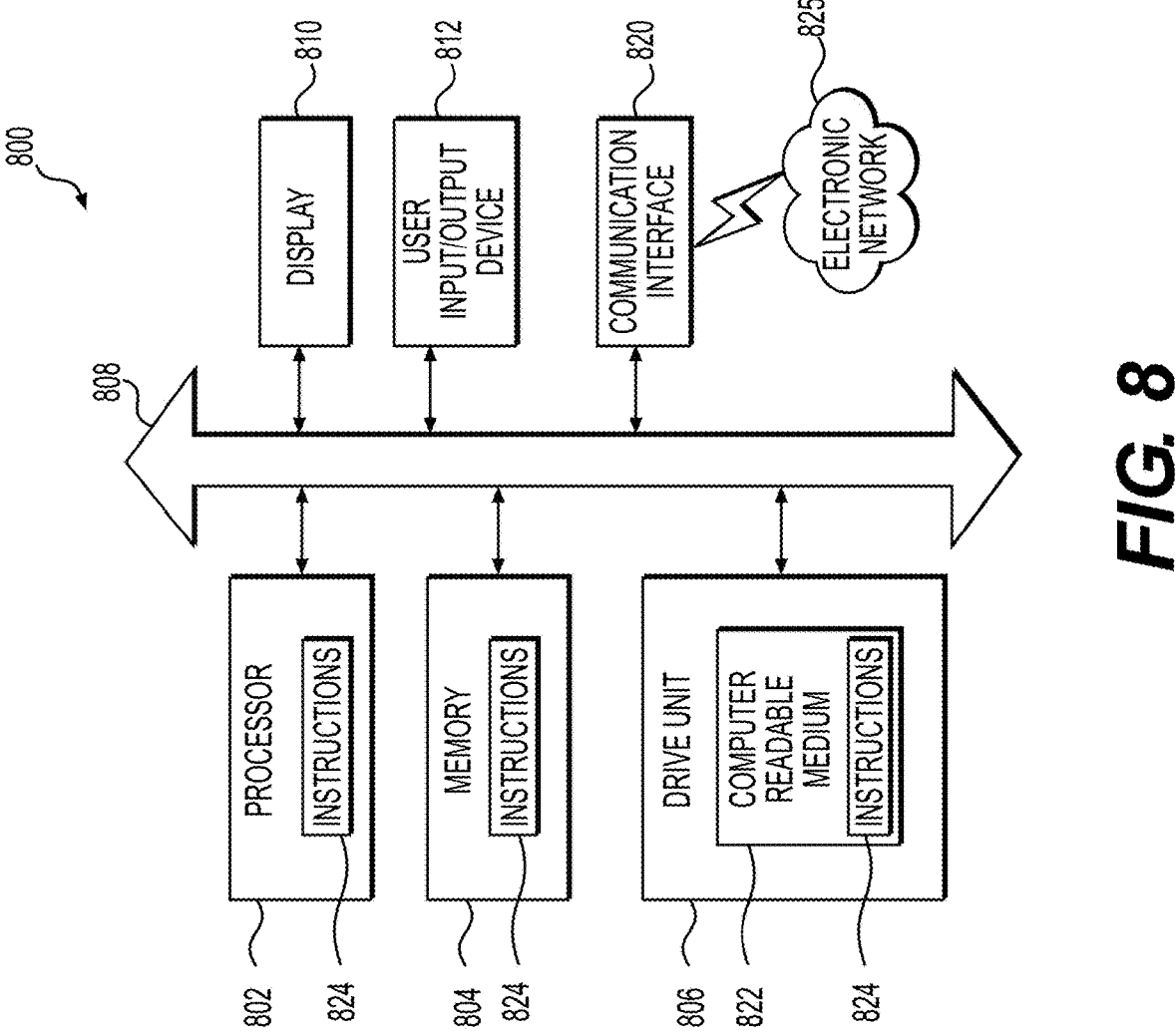
FIG. 8 depicts an example of a computing device.

FIG. 8 depicts an example of computer 800. FIG. 8 is a simplified functional block diagram of a computer 800 that may be configured as a device for executing processes or operations depicted in, or described with respect to, FIGS. 1-7C and, according to exemplary embodiments of the present disclosure. For example, the computer 800 may be configured as one of computing device 110, controller 107 of position sensing system 106, processing unit of ultrasound imaging console 116 and/or another device according to exemplary embodiments of this disclosure. In various embodiments, any of the systems herein may be a computer 800 including, e.g., a data communication interface 820 for packet data communication. The computer 800 may communicate with one or more other computers 800 using the electronic network 825. The electronic network 825 may include a wired or wireless network similar to the network 130 depicted in FIG. 1.

The computer 800 also may include a central processing unit ("CPU"), in the form of one or more processors 802, for executing program instructions 824. The program instructions 824 may include instructions for running the application on computing device 110 (e.g., if the computer 800 is computing device 110). The program instructions 824 may include instructions for running one or more operations for generating ultrasound images (e.g., if the computer 800 is a processing unit of ultrasound imaging console 116 of imaging system 104). The program instructions 824 may include instructions for running one or more operations for position and/or orientation determinations (e.g., if the computer 800 is controller 107 of position sensing system 106). The computer 800 may include an internal communication bus 808, and a drive unit 806 (such as read-only memory (ROM), hard disk drive (HDD), solid-state disk drive (SDD), etc.) that may store data on a computer readable medium 822, although the computer 800 may receive programming and data via network communications. The computer 800 may also have a memory 804 (such as random-access memory (RAM)) storing instructions 824 for executing techniques presented herein, although the instructions 824 may be stored temporarily or permanently within other modules of computer 800 (e.g., processor 802 and/or computer readable medium 822). The computer 800 also may include user input and output ports 812 and/or a display 810 to connect with input and output devices such as keyboards, mice, touchscreens, monitors, displays, etc. The various system functions may be implemented in a distributed fashion on a number of similar platforms, to distribute the processing load. Alternatively, the systems may be implemented by appropriate programming of one computer hardware platform.

Program aspects of the technology may be thought of as "products" or "articles of manufacture" typically in the form of executable code and/or associated data that is carried on or embodied in a type of machine-readable medium. "Storage" type media include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, e.g., may enable loading of the software from one computer or processor into another. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links, or the like, also may be considered as media bearing the software. As used herein, unless restricted to non-transitory, tangible "storage" media, terms such as computer or machine "readable medium" refer to any medium that participates in providing instructions to a processor for execution.

While principles of this disclosure are described herein with the reference to illustrative examples for particular applications, it should be understood that the disclosure is not limited thereto. Those having ordinary skill in the art and access to the teachings provided herein will recognize additional modifications, applications, and substitution of equivalents all fall within the scope of the examples described herein. Accordingly, the invention is not to be considered as limited by the foregoing description.

The invention claimed is:

1. A medical device, comprising:
a handle; and
a needle extending distally from the handle, wherein the needle is configured to be at least partially inserted into a body, and wherein the needle includes:
  a sheath;
  a core disposed in the sheath, the core having:
    a distal portion including a distal tip; and
    a proximal portion distinct from the distal portion, wherein a proximal end of the distal portion is coupled to a distal end of the proximal portion at a first location and a second location along an axial length of the core to define a cavity between the proximal end of the distal portion and the distal end of the proximal portion, the cavity extending between the first location and the second location; and
  a device of a position sensing system arranged in the cavity, wherein the device is one of a transmitter device or a receiver device, and the position sensing system is configured to determine a position or an orientation of the distal tip.

2. The medical device of claim 1, wherein an interior surface of the proximal end of the distal portion of the core includes one or more interlocking features corresponding to one or more structural features of the distal end of the proximal portion to couple the distal portion to the proximal portion at each of the first location and the second location.

3. The medical device of claim 1, wherein the sheath and the core are independently retractable into the handle, and only a distal end of the distal portion of the core is exposed when the sheath is retracted proximally into the handle.

4. The medical device of claim 1, wherein the device of the position sensing system is arranged in the cavity at a known distance and position relative to the distal tip.

5. The medical device of claim 1, wherein the device of the position sensing system is the receiver device, the receiver device comprising a magnetic field sensor configured to detect a magnetic field generated by an external transmitter device of the position sensing system, and provide a signal that indicates at least one of the position or the orientation of the distal tip based on a strength of the magnetic field detected.

6. The medical device of claim 1, wherein the device of the position sensing system is the transmitter device, and the transmitter device is configured to generate a magnetic field detectable by an external receiver device of the position sensing system, the external receiver device configured to provide a signal that indicates at least one of the position or the orientation of the distal tip based on a strength of the magnetic field detected.

7. The medical device of claim 1, wherein a proximal end of the proximal portion of the core is hollow to receive and direct wires of the device of the position sensing system into the handle.

8. The medical device of claim 7, wherein the handle includes an interposer board to which the wires are connected, the interposer board relaying signals between the wires and a controller of the position sensing system via an external cable connecting the interposer board and the controller.

9. The medical device of claim 7, wherein the handle includes a compartment for receiving the wires of the device of the position sensing system from the proximal end of the proximal portion of the core.

10. The medical device of claim 1, wherein the sheath and the core are independently retractable into the handle, and the handle includes a switch configured to detect when the core is in a retracted position in the handle.

11. The medical device of claim 10, wherein when the switch detects the core is in the retracted position, signals are provided to a computing device to cause generation and display of a graphical user interface, the graphical user interface comprising at least a projected needle trajectory for the needle that is overlaid on an image of a target area within the body.

12. The medical device of claim 11, wherein once the needle is at least partially inserted in the body, the graphical user interface is updated to further include at least one of the position or the orientation of the distal tip and a projected trajectory of the distal tip to the target area when the needle is advanced distally from the retracted position.

13. The medical device of claim 1, wherein the medical device is a component of a system further comprising the position sensing system and an ultrasound imaging system configured to generate ultrasound images in an ultrasound imaging plane, wherein the ultrasound imaging system comprises:

an ultrasound imaging console; and an ultrasound probe, wherein another device of the position sensing system that is one of another transmitter device or another receiver device is attachable to the ultrasound probe for determining at least one of the position or the orientation of the distal tip relative to the ultrasound imaging plane.

14. The medical device of claim 13, wherein:

when the device of the position sensing system arranged in the cavity is the receiver device, the another device of the position sensing system attached to the ultrasound probe is the another receiver device; and when the device of the position sensing system arranged in the cavity is the transmitter device, the another device of the position sensing system attached to the ultrasound probe is the another transmitter device.

15. A medical device, comprising:

a needle configured to be at least partially inserted into a body, the needle including:

a sheath;

a core disposed in the sheath, the core having:

a distal portion including a distal tip and a proximal end, an interior surface of the proximal end of the distal portion comprising one or more interlocking features; and a proximal portion distinct from the distal portion, wherein the proximal end of the distal portion is coupled to a distal end of the proximal portion via the one or more interlocking features to define a cavity between the proximal end of the distal portion and the distal end of the proximal portion; and a device of a position sensing system arranged in the cavity, wherein the device is one of a transmitter device or a receiver device, and the position sensing system is configured to determine a position or an orientation of the distal tip;

wherein a proximal end of the proximal portion of the core is hollow to receive and proximally direct wires of the device of the position sensing system; and a handle from which the needle extends distally, the handle including a compartment for receiving the wires of the device of the position sensing system proximally directed from the core.

16. The medical device of claim 15, wherein the handle further includes an interposer board to which the wires of the device of the position sensing system are connected, the interposer board relaying signals between the wires and a controller of the position sensing system via an external cable connecting the interposer board and the controller.

17. The medical device of claim 16, wherein the sheath and the core are independently retractable into the handle, and the handle further includes a switch connected to the interposer board, the switch configured to detect when the core is in a retracted position in the handle.

18. A medical device, comprising:

a handle; and a needle extending distally from the handle, wherein the needle is configured to be at least partially inserted into a body toward a target area, and wherein the needle includes:

a sheath;

a core disposed in the sheath, the core having:

a distal portion including a distal tip; and a proximal portion distinct from the distal portion, wherein a distal end of the proximal portion comprises a cavity extending an axial length of the distal end of the proximal portion, and wherein a proximal end of the distal portion is coupled to the distal end of the proximal portion to enclose the cavity between the proximal end of the distal portion and the distal end of the proximal portion; and a device of a position sensing system arranged in the cavity, wherein the device is one of a transmitter device or a receiver device, and the position sensing system is configured to determine a position or an orientation of the distal tip;

wherein the needle is configured to be in a retracted position within the handle when the needle is at least partially inserted into the body toward the target area; and wherein the medical device is in communication with a computing device configured to:

determine, based on at least one of the position or the orientation of the distal tip, a projected trajectory of the distal tip to the target area when the needle is advanced distally from the retracted position; and generate a graphical user interface overlaying at least one of the position or the orientation of the distal tip and the projected trajectory on an image of the target area for display.

19. The medical device of claim 18, wherein the medical device and the computing device are components of a system comprising the position sensing system and an ultrasound imaging system configured to generate the image of the target area in an ultrasound imaging plane, wherein the position sensing system includes another device that is one of another transmitter device or another receiver device, and wherein the ultrasound imaging system comprises:

an ultrasound imaging console; and an ultrasound probe, wherein the another device of the position sensing system is attachable to the ultrasound probe for determining at least one of the position or the orientation of the distal tip relative to the ultrasound imaging plane.

20. The medical device of claim 1, wherein each of the sheath and the core is independently retractable into the handle, and wherein an extent of proximal retraction of the sheath into the handle, relative to the core, is mechanically limited such that the sheath does not extend proximally past the distal end of the distal portion of the core.

* * * * *